United States Patent
Midha et al.

(10) Patent No.: US 7,297,697 B2
(45) Date of Patent: Nov. 20, 2007

(54) 4-(DIARYLMETHYL)-1-PIPERAZINYL DERIVATIVES

(75) Inventors: Ajay Sohanlal Midha, Baroda (IN); Hemant Ashvinbhai Chokshi, Baroda (IN); Trinadha Rao Chitturi, Baroda (IN); Rajamannar Thennati, Baroda (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 351 days.

(21) Appl. No.: 10/509,052

(22) PCT Filed: Mar. 27, 2003

(86) PCT No.: PCT/IN03/00089

§ 371 (c)(1), (2), (4) Date: Dec. 29, 2004

(87) PCT Pub. No.: WO03/079970

PCT Pub. Date: Oct. 2, 2003

(65) Prior Publication Data

US 2005/0107393 A1   May 19, 2005

(30) Foreign Application Priority Data

Mar. 27, 2002   (IN) .................... 302/MUM/2002

(51) Int. Cl.
 A61K 31/50   (2006.01)
 A61K 31/501   (2006.01)
 C07D 241/04   (2006.01)
 C07D 295/00   (2006.01)

(52) U.S. Cl. ............... 514/252.12; 544/358; 544/398

(58) Field of Classification Search ............ None
See application file for complete search history.

(56) References Cited

U.S. PATENT DOCUMENTS 4,525,358 A   6/1985   Baltes et al.

FOREIGN PATENT DOCUMENTS

| EP | 0 598 123 A1 | 5/1994 |
|---|---|---|
| FR | 2.082.168 | 12/1971 |
| JP | 07138230 | * 5/1995 |
| WO | 00/58295 | 10/2000 |
| WO | 01/29016 A1 | 4/2001 |
| WO | 01/79188 A1 | 10/2001 |

* cited by examiner

Primary Examiner—Zachary C. Tucker
Assistant Examiner—Erich Leeser

(74) Attorney, Agent, or Firm—Merchant & Gould P.C.

(57) ABSTRACT

A compound of formula I

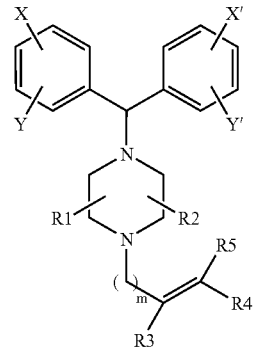

Formula I wherein X, Y, X' & Y' are selected from hydrogen, halogen, substituted or unsubstituted alkyl (linear, branched or cyclo), aryl, alkyloxy and haloalkyl group; $R_1$, $R_2$, $R_3$ & $R_4$ are selected from hydrogen, substituted or unsubstituted alkyl groups (linear, branched or cyclo), aryl, heteroaryl groups or aralkyl groups, heterocycles containing one or more of hetero atoms (viz., N, S, O), substituted or unsubstituted alkenyl or alkynyl groups of carbon 2 to 6; wherein the substituents $R_1$ & $R_2$ on the piperazinyl moiety are either syn or anti to each other and optionally $R_3$ and $R_4$ together with the carbons to which they are attached form a monocyclic saturated or aryl or substituted aryl or heteroaryl or substituted heteroaryl ring containing one or more hetero atoms selected from N, S and O with a ring size ranging from 3 to 6; with a proviso that when $R_3$ & $R_4$ together do not form part of a ring they may exist in either E or Z configuration; $R_5$ is $(CH_2)_n$—O—$CH_2$—CO-Z wherein n is 1 to 6; Z is selected from OH, OR, NRR', N(OR)R', N(R)—N(R)R'and

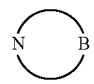

wherein R & R' are selected from hydrogen, substituted or unsubstituted alkyl groups (linear, branched or cyclo), aryl, heteroaryl groups or aralkyl groups, heterocycles containing one or more of hetero atoms (viz., N, S, O), substituted or unsubstituted alkenyl or alkynyl groups of carbon 2 to 6; and B is selected from —$(CH_2)n$-(n is 1 to 6) and —$(CH_2)x$-D-$(CH_2)y$ where D is O, NR, S or SO2, x and y are independently 1 to 6; and m is selected from 1 to 6; and pharmaceutically acceptable salts thereof.

19 Claims, No Drawings

4-(DIARYLMETHYL)-1-PIPERAZINYL DERIVATIVES

The present invention relates to compound of formula I, 4-(diarylmethyl)-1-piperazinyl derivatives with alkenyl moiety substituted at the 1-position of the piperazine unit.

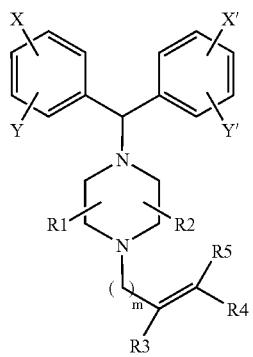

Formula I wherein X, Y, X' & Y' are selected from hydrogen, halogen, substituted or unsubstituted alkyl (linear, branched or cyclo), aryl, alkyloxy and haloalkyl group; $R_1$, $R_2$, $R_3$ & $R_4$ are selected from hydrogen, substituted or unsubstituted alkyl groups (linear, branched or cyclo), aryl, heteroaryl groups or aralkyl groups, heterocycles containing one or more of hetero atoms (viz., N, S, O), substituted or unsubstituted alkenyl or alkynyl groups of carbon 2 to 6 wherein the substituents $R_1$ & $R_2$ on the piperazinyl moiety are either syn or anti to each other and optionally $R_3$ and $R_4$ together with the carbons to which they are attached form a monocyclic saturated or aryl or substituted aryl or heteroaryl or substituted heteroaryl ring containing one or more hetero atoms selected from N, S and O with a ring size ranging from 3 to 6; with a proviso that when $R_3$ & $R_4$ together do not form part of a ring they may exist in either E or Z configuration; $R_5$ is $(CH_2)_n$—O—$CH_2$—CO-Z wherein n is 1 to 6; Z is selected from OH, OR, NRR', N(OR)R', N(R)—N(R)R' and

wherein R & R' are selected from hydrogen, substituted or unsubstituted alkyl groups (linear, branched or cyclo), aryl, heteroaryl groups or aralkyl groups, heterocycles containing one or more of hetero atoms (viz., N, S, O), substituted or unsubstituted alkenyl or alkynyl groups of carbon 2 to 6 and B is selected from —(CH2)n- (n is 1 to 6) and —(CH2)x-D-(CH2)y where D is O, NR, S or SO2, x and y are independently 1 to 6; and m is selected from 1 to 6; and pharmaceutically acceptable salts thereof.

The $R_5$ group in formula I represents an alkyloxy acetic acid and its derivatives, such as an ester, an amide, a hydroxamic acid or a hydrazide. These compounds include their non-toxic pharmaceutically acceptable acid addition salts and those derived from alkali metals, alkaline earth metals or amines including hydroxyalkyl and polyhydroxyalkyamines amines.

The compound of the present invention is an antihistaminic compound useful in the treatment of histamine mediated diseases.

PRIOR ART

U.S. Pat. No. 4,525,358 (Indian reference not available) discloses an antihistaminic compound cetirizine

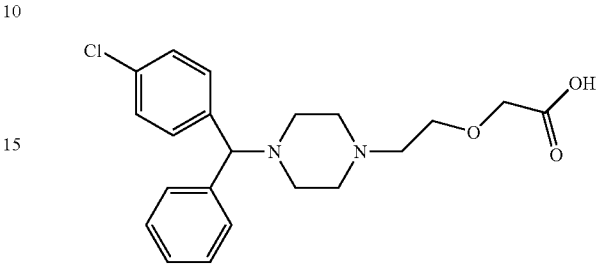

which is used as an antiallergic, antihistaminic, bronchodilator or antispasmodic agent. It is useful in patients suffering from indications requiring the above mentioned effects. However, it is devoid of an olefinic side chain on the piperazine ring.

PCT publication WO 01/79188 discloses novel compounds of formula

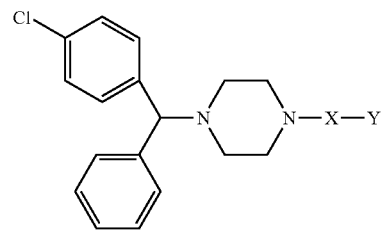

which are more hydrophobic in nature than cetirizine as Y is substituted or unsubstituted carbocyclic, a heterocyclic, a polycyclic hydrocarbonyl, a heteropolycyclic, a carbocyclic arenyl, a heteropolycyclic arenyl or theophylline group.

PCT publication WO 00/58295 discloses new compounds of formula

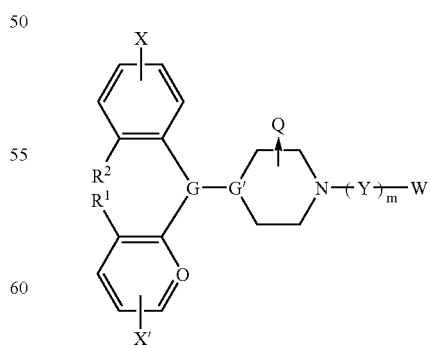

for treating asthma, allergy and inflammatory disorders, wherein W or a substituent on the phenyl ring is a hydroxylamine.

European patent number 598123 discloses piperazine derivatives of formula

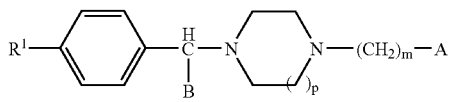

which are different from compound of formula I as they do not contain an olefinic side chain on the piperazine ring.

We have now found novel antihistaminic compounds.

OBJECTS OF THE INVENTION

The object of the present invention is to provide antihistaminic compound of formula I and pharmaceutically acceptable salts thereof.

SUMMARY OF INVENTION

A compound of formula I

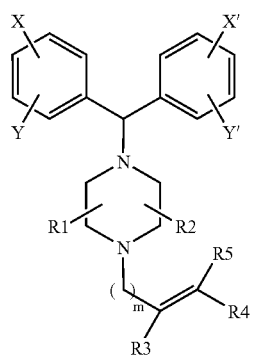

Formula I wherein X, Y, X' & Y' are selected from hydrogen, halogen, substituted or unsubstituted alkyl (linear, branched or cyclo), aryl, alkyloxy and haloalkyl group; $R_1$, $R_2$, $R_3$ & $R_4$ are selected from hydrogen, substituted or unsubstituted alkyl groups (linear, branched or cyclo), aryl, heteroaryl groups or aralkyl groups, heterocycles containing one or more of hetero atoms (viz., N, S, O), substituted or unsubstituted alkenyl or alkynyl groups of carbon 2 to 6 wherein the substituents $R_1$ & $R_2$ on the piperazinyl moiety are either syn or anti to each other and optionally $R_3$ and $R_4$ together with the carbons to which they are attached form a monocyclic saturated or aryl or substituted aryl or heteroaryl or substituted heteroaryl ring containing one or more hetero atoms selected from N, S and O with a ring size ranging from 3 to 6; with a proviso that when $R_3$ & $R_4$ together do not form part of a ring they may exist in either E or Z configuration;

$R_5$ is $(CH_2)_n$—O—$CH_2$—CO-Z wherein n is 1 to 6; Z is selected from OH, OR, NRR', N(OR)R', N(R)—N(R)R' and

wherein R & R' are selected from hydrogen, substituted or unsubstituted alkyl groups (linear, branched or cyclo), aryl, heteroaryl groups or aralkyl groups, heterocycles containing one or more of hetero atoms (viz., N, S, O), substituted or unsubstituted alkenyl or alkynyl groups of carbon 2 to 6 and B is selected from —(CH2)n- (n is 1 to 6) and —(CH2)x-D-(CH2)y where D is O, NR, S or SO2, x and y are independently 1 to 6; and m is selected from 1 to 6; and pharmaceutically acceptable salts thereof

DETAILED DESCRIPTION OF THE INVENTION

Accordingly, the present invention provides compound of formula I

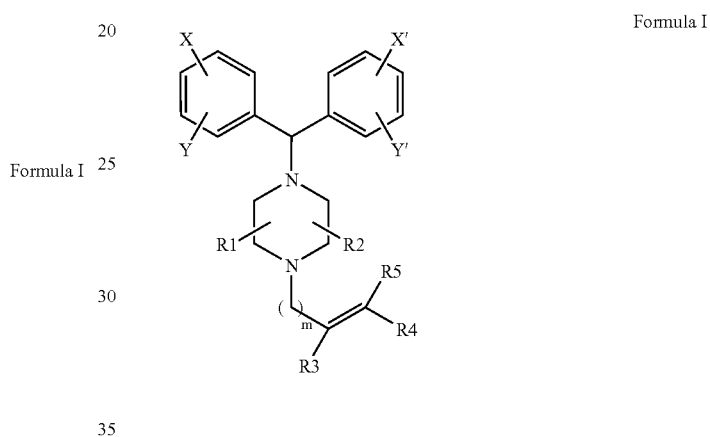

Formula I wherein X, Y, X' & Y' are selected from hydrogen, halogen, substituted or unsubstituted alkyl (linear, branched or cyclo), aryl, alkyloxy and haloalkyl group; $R_1$, $R_2$, $R_3$ & $R_4$ are selected from hydrogen, substituted or unsubstituted alkyl groups (linear, branched or cyclo), aryl, heteroaryl groups or aralkyl groups, heterocycles containing one or more of hetero atoms (viz., N, S, O), substituted or unsubstituted alkenyl or alkynyl groups of carbon 2 to 6 wherein the substituents $R_1$ & $R_2$ on the piperazinyl moiety are either syn or anti to each other and optionally $R_3$ and $R_4$ together with the carbons to which they are attached form a monocyclic saturated or aryl or substituted aryl or heteroaryl or substituted heteroaryl ring containing one or more hetero atoms selected from N, S and O with a ring size ranging from 3 to 6; with a proviso that when $R_3$ & $R_4$ together do not form part of a ring they may exist in either E or Z configuration;

$R_5$ is $(CH_2)_n$—O—$CH_2$—CO-Z wherein n is 1 to 6; Z is selected from OH, OR, NRR', N(OR)R', N(R)—N(R)R' and

wherein R & R' are selected from hydrogen, substituted or unsubstituted alkyl groups (linear, branched or cyclo), aryl, heteroaryl groups or aralkyl groups, heterocycles containing one or more of hetero atoms (viz., N, S, O), substituted or unsubstituted alkenyl or alkynyl groups of carbon 2 to 6 and B is selected from —(CH2)n- (n is 1 to 6) and —(CH2)x-D-(CH2)y where D is O, NR, S or SO2, x and y are independently 1 to 6; and m is selected from 1 to 6; and pharmaceutically acceptable salts thereof.

The compound of the present invention wherein $R_3$ and $R_4$ together with the carbons to which they are attached form a ring system A (formula II), wherein A is selected from monocyclic saturated or aryl or substituted aryl or heteroaryl or substituted heteroaryl ring containing one or more hetero atoms selected from N, S and O with a ring size ranging from 3 to 6 is referred to herein as compound of formula II

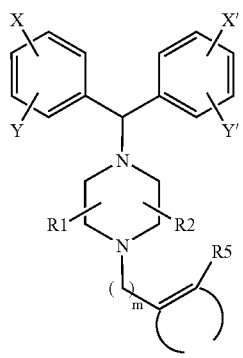

formula II

The preferred compound of formula II is wherein the ring is a benzene ring

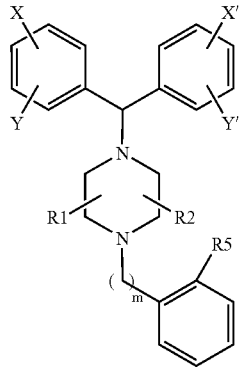

formula II

The compound of the present invention wherein $R_3$ and $R_4$ are in E configuration, is referred to herein as compound of formula III,

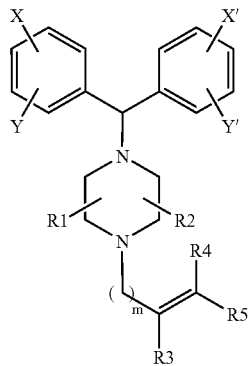

formula III

Preferably, compound of formula I wherein
X, Y, X' & Y' are selected from hydrogen, chloro and fluoro;
$R_1$ and $R_2$, are hydrogen;
$R_3$ and $R_4$ are hydrogen existing in the E or Z configuration or optionally $R_3$ and $R_4$ together with the carbons to which they are attached form a benzene ring; and
$R_5$ is $CH_2$—O—$CH_2$—CO-Z wherein Z is selected from OH and OR wherein R may be selected from methyl, ethyl and isopropyl;
and m is 1.

Compounds of the present invention may be prepared using different routes. For instance, as illustrated in Schemes 1 to 4.

In process as illustrated in Scheme 1

Scheme 1

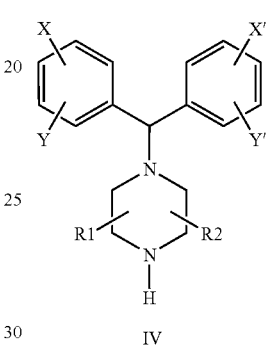 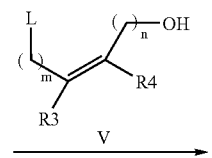

IV                                          V

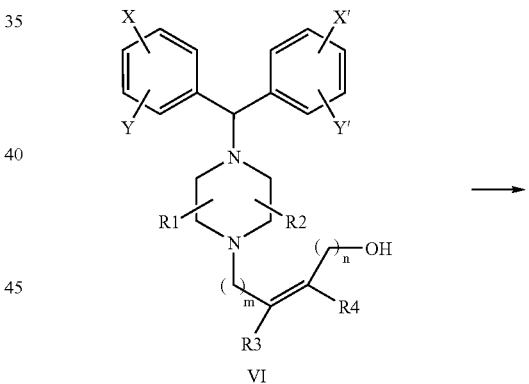

VI

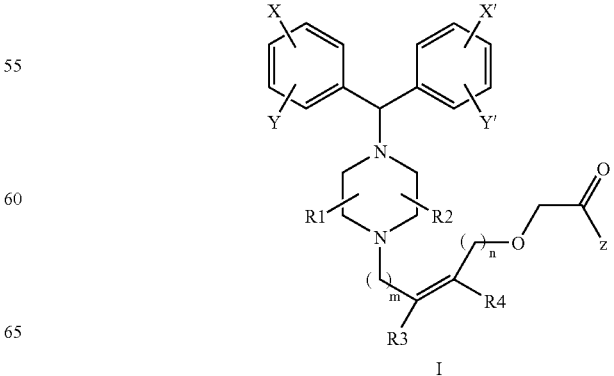

I compound of formula IV,

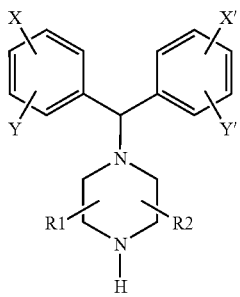

formula IV wherein X, Y, X', Y', R₁ and R₂ are as described above, is N-alkylated with compound of formula V wherein L is a leaving group selected from halo, or an alkyl or arylsulfonate group for e.g. methanesulfonate or p-toluenesulfonate and the like, to give compound of formula VI,

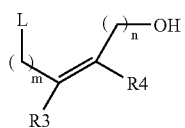

formula V

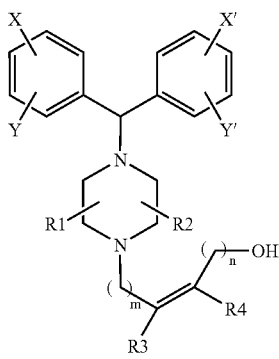

formula VI which is then reacted with $X_1CH_2COZ$ wherein $X_1$ is halo group such as chloro to yield compound of formula I.

The starting material, compound of formula IV, may be prepared by known prior art such as Baltzly, R. et al, J. Org. Chem., 14, 775, 1949; Yung, D. K et al J. Pharm. Sci., 67(7), 1978.

In process as illustrated in Scheme 2,

Scheme 2

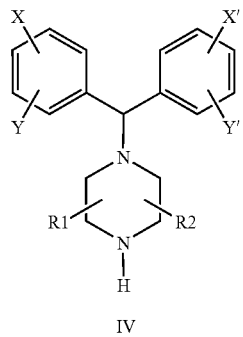 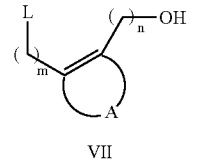

IV

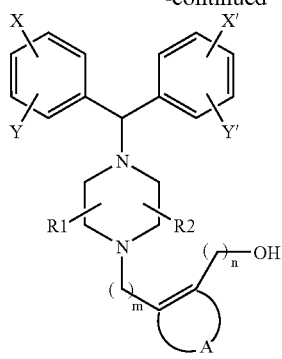 

VIII

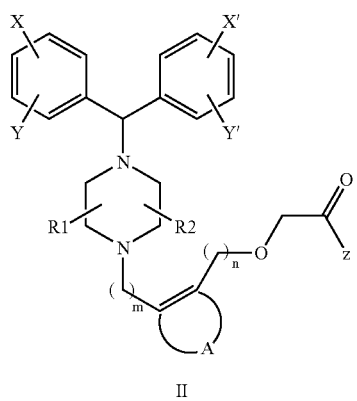

II compound of formula I wherein R₃ and R₄ together form ring selected from cyclic, aryl or substituted aryl, heterocyclic aryl groups or substituted heterocyclic aryl groups containing one or more hetero atoms (viz., N, S, O) with a ring size ranging from 3 to 6, referred to herein as compound of formula II may be prepared by a process similar to that described above wherein compound of formula IV is N-alkylated with compound of formula VII wherein L is a leaving group selected from halo, or an alkyl or arylsulfonate group for e.g. methanesulfonate or p-toluenesulfonate and the like, to give compound of formula VIII,

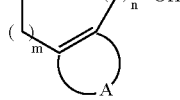

formula VII

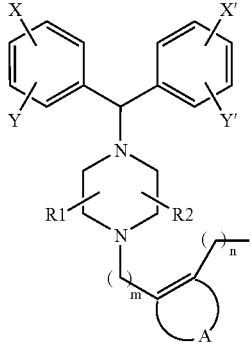

formula VIII which is then reacted with $X_1CH_2COZ$ wherein $X_1$ is halo group such as chloro to yield compound of formula I.

In process as illustrated in Scheme 3,

Scheme 3

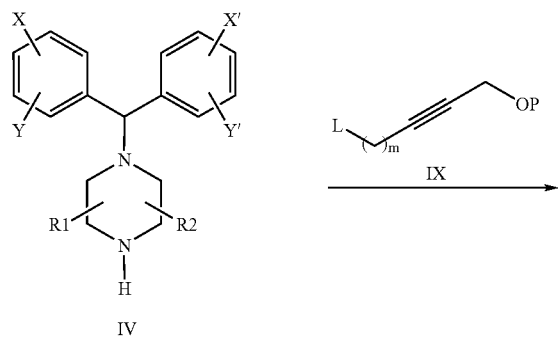

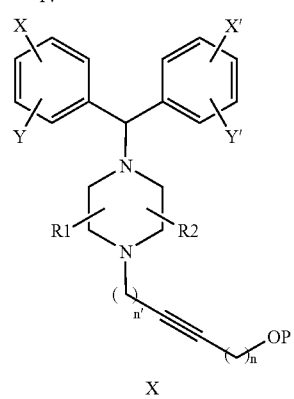

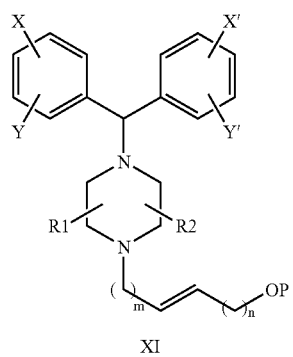

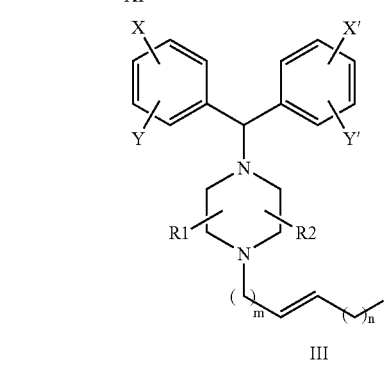

compound of formula I wherein $R_3$ and $R_4$ are hydrogen and in E or Z configuration, may be prepared by N-alkylating compound of formula IV with compound of formula IX,

formula IX

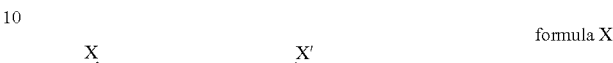

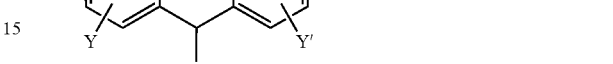

formula X

wherein P maybe H or any protecting group such as acetate to give compound of formula X, which is reduced to give compound of formula XI. Compound of formula XI is then reacted, after removing the protecting group wherever required, with $X_1CH_2COZ$ wherein $X_1$ is halo group such as chloro to yield compound of formula I.

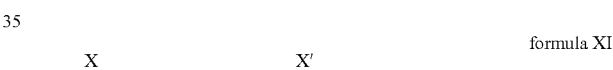

formula XI

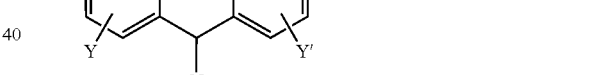

In process as illustrated in Scheme 4,

Scheme 4

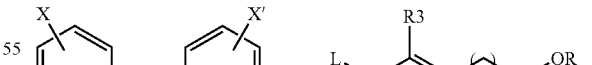

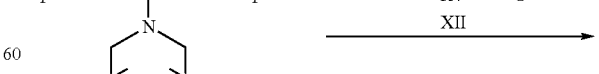

-continued

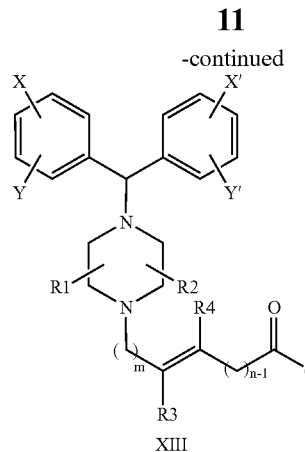

XIII

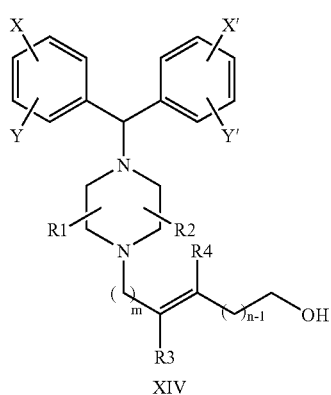

XIV

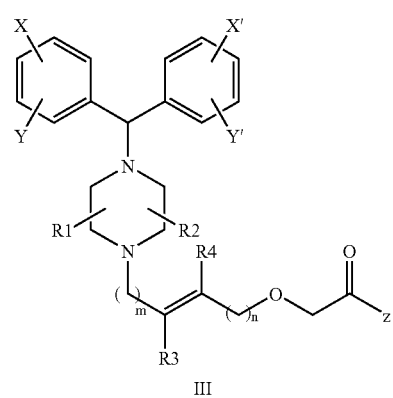

III compound of formula I wherein $R_3$ and $R_4$ are in E configuration may be prepared by N-alkylating compound of formula IV with compound of formula XII to give compound of formula XIII which is then reduced to yield compound of formula XIV.

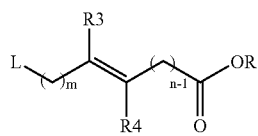

formula XII formula XIII

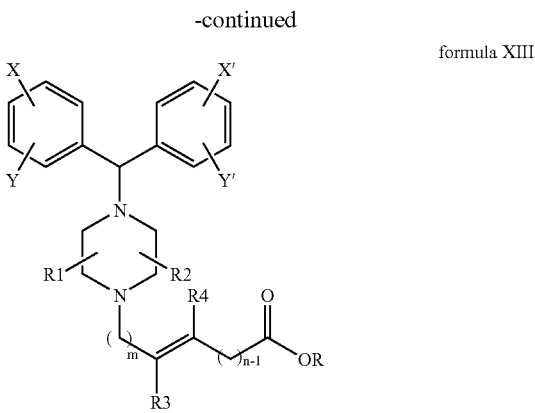

Compound of formula XIV is treated with $X_1CH_2COZ$ wherein $X_1$ is halo group such as chloro to yield compound of formula I.

formula XIV

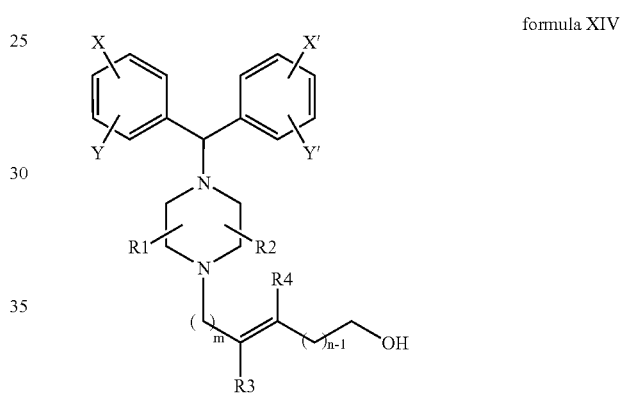

Another aspect of the present invention relates to formulation of compound of formula I in suitable form, which can be administered to the patient.

Compounds of the present invention can be provided as a pharmaceutical composition for use in the treatment of histamine mediated diseases. The composition comprises compound of formula I and pharmaceutically acceptable ingredients.

Such compositions may be prepared by admixing compound of formula I and pharmaceutically acceptable ingredients. Usually the compositions are adapted for oral administration. However, they may be adapted for other modes of administration, for example parenteral administration, sublingual, transdermal or opthalmic administration.

The compositions may be in the form of tablets, capsules, powders, granules, nasal spray, aerosols, lozenges, ointments, creams, transdermal patches, reconstitutable powders, or liquid preparations, such as oral or sterile solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The compositions are preferably in a unit dosage form in an amount appropriate for the relevant daily dosage.

The solid oral compositions may be prepared by conventional methods of blending, filling or tabletting known to those skilled in this art. Repeated blending operations may be used to distribute the active agent throughout those compositions employing large quantities of fillers. Such operations are of course conventional in the art. The tablets may be coated according to methods well known in normal pharmaceutical practice.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavoring or coloring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agent can be dissolved in the vehicle. To enhance the stability, the composition can be frozen after filling into the vial and the water removed under vacuum.

For ophthalmic administration, sterile solution or suspension can be prepared. Ophthalmic solution can be prepared by dissolving the compound in water for injection along with suitable preservative, chelating agent, osmogen, viscosity enhancing agent, antioxidant and buffering agent. Solution is aseptically filtered and filled into suitable vials or bottles of suitable material. Similarly suspension can be prepared by aseptically dispersing the sterile compound in a sterile aqueous vehicle containing suitable preservative, chelating agent, osmogen, suspending agent, anti-oxidant and buffering agent. Preservative-free unit doses can also be prepared in similar way for solution as well as suspension and aseptically filled into unit dose containers.

Compositions may contain from 0.1% to 99.0% by weight, preferably from 10-60% by weight, of the active material, depending upon the method of administration.

Composition may, if desired, be in the form of a pack accompanied by written or printed instructions for use.

The compound of formula I on being formulated is useful for various histamine mediated diseases. $IC_{50}$ was determined for the compounds prepared by the present invention.

EXAMPLES

Example 1

4-{4-[Bis-(4-fluorophenyl)methyl]piperazin-1-yl}-(Z)-but-2-en-1-ol, (VIa, X=X'=4-F; Y=Y'=R1=R2=R3=R4=H; m=n=1)

A solution containing 1-[bis-(4-fluorophenyl)methyl]piperazine (140 g, 0.485 mol), toluene (700 ml), 4-chloro-2-butene-1-ol (67.25 g, 0.631), and diisopropylethylamine (125.8 g, 0.971 mol) is stirred at 47-49° C. for 5 hrs. Water (350 ml) is added to the reaction mixture, the organic layer separated and the aqueous layer extracted with dichloromethane (2×200 ml). The combined organic layer is washed with water (200 ml), and concentrated to obtain crude product which is purified by flash column chromatography on silica gel using dichloromethane-methanol (9.6:0.4) as mobile phase to obtain pure product.

$^1$H-NMR (CDCl$_3$, δppm): 2.15-2.80 (m, 8H), 3.01 (d, J=4.90 Hz, 2H), 4.13 (d, J=3.96 Hz, 2H), 4.20 (s, 1H), 5.55-5.75 (m, 1H), 5.75-6.00 (m, 1H), 6.96 (t, J=8.14 Hz, 4H), 7.20-7.40 (m, 4H).

Example 2

(R,S)-4-{4[(4-chlorophenyl)phenylmethyl]piperazin-1-yl}-(Z)-but-2-en-1-ol, [VIb(R,S), X=Cl; X'=Y=Y'=R1=R2=R3=R4=H; m=n=1]

(R,S)-1-[(4-chlorophenyl)phenylmethyl]piperazine 8.0 g (mol) is converted to (R,S)-4-{4-[(4-chlorophenyl)phenylmethyl]piperazin-1-yl}-(Z)-but-2-en-1-ol in a manner similar to example 1. Crude product is obtained as a syrupy mass, which is purified by flash column chromatography on silica gel using toluene-methanol (9:1) as mobile phase to obtain pure product.

$^1$H-NMR (CDCl$_3$, δppm): 2.10-2.90 (m, 8H), 3.01 (d, J=5.75 Hz, 2H), 4.13 (d, J=−5.25 Hz, 2H), 4.19 (s, 1H), 5.50-5.75 (m, 1H), 5.75-6.00 (m, 1H), 7.00-7.40 (m, 9H).

Example 3

4-{4-Benzhydrylpiperazin-1-yl}-(Z)-but-2-en-1-ol, (VIc, X=X'=Y=Y'=H; R1=R2=R3=R4=H; m=n=1)

A solution containing 1-benzhydrylpiperazine (3 g, 0.0119 mol), toluene (20 ml), 4-chloro-2-butene-1-ol (1.65 g, 0.0155 mol), diisopropylethylamine (3.81 g, 0.0295 mol), and DMF (3 ml) is stirred at 55-60° C. for 5 hrs. The reaction mass is quenched with water (20 ml), organic layer separated and the aqueous layer extracted with dichloromethane (2×20 ml). The organic extract is washed with water (10 ml), and concentrated to obtain crude product, which is purified by flash column chromatography on silica gel using dichloromethane-methanol (9.3:0.7) as mobile phase to obtain pure product.

$^1$H-NMR (CDCl$_3$, δppm): 2.10-2.80 (m, 8H), 3.01 (d, J=5.52 Hz, 2H), 4.13 (dd, J$_1$=5.19 Hz, J$_2$=0.68 Hz, 2H), 4.21 (s, 1H), 5.50-5.75 (m, 1H), 5.75-6.00 (m, 1H), 7.00-7.50 (m, 10H).

Example 4

4-{4-[Bis-(2,4-difluorophenyl)methyl]piperazin-1-yl}-(Z)-but-2-en-1-ol, (VId, X=X'=Y=Y'=F; R1=R2=R3=R4=H; m=n=1)

1-[Bis-(2,4-difluorophenyl)methyl]piperazine (20.0 g, 0.0617 mol) is converted to 4-{4-[bis-(2,4-difluorophenyl)methyl]piperazin-1-yl}-(Z)-but-2-en-1-ol in a manner similar to example 1. Crude product is obtained as a syrupy mass, which is purified by flash column chromatography on silica gel using toluene-methanol (9:1) as mobile phase to obtain pure product.

$^1$H-NMR (CDCl$_3$, δppm): 2.20-2.85 (m, 8H), 3.02 (dd, J$_1$=6.00 Hz, J$_2$=0.74 Hz, 2H), 4.14 (dd, J$_1$=5.31 Hz, J$_2$=0.98 Hz, 2H), 4.94 (s, 1H), 5.50-5.75 (m, 1H), 5.75-6.00 (m, 1H), 6.55-7.00 (m, 4H), 7.30-7.60 (m, 2H).

Example 5

4-{4-[Bis-(4-chlorophenyl)methyl]piperazin-1-yl}-(Z)-but-2-en-1-ol, (VIe, X=X'=Cl; Y=Y'=R1=R2=R3=R4=H; m=n=1)

1-[Bis-(4-chlorophenyl)methyl]piperazine (5.044 g, mol) is converted to 4-{4-[bis-(4-chlorophenyl)methyl]piperazin-1-yl}-(Z)-but-2-en-1-ol in a manner similar to example 1. The crude product obtained is purified by flash column chromatography on silica gel using toluene-methanol (9:1) as mobile phase to obtain pure product.

$^1$H-NMR (CDCl$_3$, δppm): 2.10-2.80 (m, 8H), 3.01 (d, J=5.87 Hz, 2H), 4.13 (dd, J$_1$=5.26 Hz, J$_2$=0.88, 2H), 4.18 (s, 1H), 5.50-5.75 (m, 1H), 5.75-6.00 (m, 1H), 7.00-7.40 (m, 8H).

Example 6

{2-{4-[Bis-(4-fluorophenyl)methyl]piperazin-1-ylmethyl}phenyl}methanol (VIIIa, X=X'=F; Y=Y'=R1=R2=H; m=n=1, A=benzene ring)

1-[Bis-(4-chlorophenyl)methyl]piperazine (5.0 g, 0.0173 mol) is converted to {2-{4-[bis-(4-fluorophenyl)methyl]piperazin-1-ylmethyl}phenyl}methanol using 2-(chloromethyl)benzyl alcohol, in a manner similar to example 1. The crude product obtained as brownish yellow syrup is purified by flash column chromatography on silica gel using toluene-methanol (9.2:0.8) as mobile phase to obtain pure product.

$^1$H-NMR (CDCl$_3$, δppm): 2.00-2.80 (m, 8H), 3.6 (s, 2H), 4.18 (s, 1H), 4.57 (s, 2H), 6.70-7.03 (m, 4H), 7.05-7.40 (m, 8H).

Example 7

{2-{4-[(4-chlorophenyl)phenylmethyl]piperazin-1-ylmethyl}phenyl}methanol, (VIIIb, X=Cl; X'=Y=Y'=R1=R2=H; m=n=1, A=benzene ring)

1-[Bis-(4-chlorophenyl)methyl]piperazine (4.0 g, 0.0140 mol) is converted to {2-{4-[(4-chlorophenyl)phenylmethyl]piperazin-1-ylmethyl}phenyl)methanol in a manner similar to example 1. The crude product obtained is purified by flash column chromatography on silica gel using toluene-methanol (9.2:0.8) as mobile phase to obtain pure product as a white foamy solid.

$^1$H-NMR (CDCl$_3$, δppm): 2.00-2.80 (m, 8H), 3.60 (s, 2H), 4.16 (s, 1H), 4.56 (s, 2H), 6.86 (br, exchangeable by D$_2$O), 6.95-7.40 (m, 13H).

Example 8

4-{4-[Bis-(4-fluorophenyl)methyl]piperazin-1-yl}but-2-yn-1-ol (Xa, X=X'=4-F; Y=Y'=R—R2=H; m=1)

Method A: Using 4-chloro-2-butyne-1-ol

To a solution containing 1-[bis-(4-fluorophenyl)methyl]piperazine (300 g, 1.040 mol), tetrahydrofuran (1800 ml) and diisopropylethylamine (242.1 g, 1.873 mol) is added dropwise 4-chloro-2-butyne-1-ol (130.5 g, 1.248 mol) during 1 hr at 10-15° C. After stirring at 10-15° C. for 1.5 hr the temperature is gradually raised to 25-30° C. and stirred for further 7 hr. Thereafter, a solution of citric acid (437.3 g, 2.08 mol) in water (500 ml) is added and the mixture is concentrated under reduced pressure at below 60° C to remove most of the solvent. The resulting aqueous mass is washed with toluene (2×400 ml), basified to pH=9-10 and the product extracted into dichloromethane (2×400 ml). The dichloromethane layer is washed with water (300 ml) and degassed to obtain crude product, which is purified by flash column chromatography on silica gel using toluene-methanol (9:1) as mobile phase.

$^1$H-NMR (CDCl$_3$, δppm): 1.84 (br, 1H, D$_2$O exchangeable), 2.20-2.80 (m, 8H), 3.31 (t, J=1.84 Hz, 2H), 4.21 (s, 1H), 4.29 (t, J=1.80 Hz, 2H), 6.80-7.05 (m, 4H), 7.10-7.50 (m, 4H).

Method B: Using 2-butyne-1,4-diol

A solution of methanesulfonyl chloride (48.69 g, 0.425 mol) and tetrahydrofuran (100 ml) is added dropwise to a stirred solution of 2-butyne-1,4-diol (10 g, 1.162 mol) and diisopropylethylamine (62.45 g, 0.483 mol) in tetrahydrofuran (400 ml) during 2 hr at 0-5° C. After 1 hr stirring at 0-5° C. for 1 hr the temperature is raised to 25-30° C. and stirred for further 1 hr. The reaction mixture is then cooled to 10-15° C., and to it is added diisopropylethylamine (99.34 g, 0.769 mol), followed by 1-[bis-(4-fluorophenyl)methyl]piperazine (110.81 g, 0.384 mol) in portions during 30 min. The reaction mass is stirred at 10-15° C. for 1 hr and then at 25-30° C. for furthers 8 hrs. Toluene (500 ml) is added to it and the contents washed with water (2×400 ml). Thereafter, a solution of citric acid (161.52 g, 0.769 mol) in water (500 ml) is added and the mixture is concentrated under reduced pressure at below 60° C. to remove most of the solvent. The resulting aqueous mass is washed with hexane (2×250 ml), basified to pH=9-10 and the product extracted into ethyl acetate (2×300 ml). The ethyl acetate layer is washed with water (200 ml) and degassed to obtain crude product which is purified by flash column chromatography on silica gel using toluene-methanol (9.3:0.7) as mobile phase to obtain pure product.

Example 9

(R,S)-4-{4-[(4-Chlorophenyl)phenylmethyl]piperazin-1-yl}but-2-yn-1-ol (by method A in Example 10), (Xb, X=Cl; X'=Y=Y'=R1=R2=H; m=1)

A solution containing (R,S)-1-[(4-chlorophenyl)phenylmethyl]piperazine (10 g, 0.0349 mol), toluene (50 ml), 4-chloro-2-butyne-1-ol (4.74 g, 0.0453 mol), and diisopropylethylamine (9.02 g, 0.0698 mol) is stirred at 45-50° C. for 6 hrs. The reaction mixture is quenched with water (20 ml). The organic layer is separated and the aqueous layer extracted with dichloromethane (2×30 ml). The organic layers is washed with water (20 ml) and concentrated to obtain crude product as a syrupy mass, which is purified by flash column chromatography on silica gel using dichloromethane-methanol (9.6:0.4) as mobile phase to obtain pure product.

$^1$H-NMR (CDCl$_3$, δppm): 1.88 (br, 1H), 2.20-2.75 (m, 8H), 3.31 (t, J=1.72 Hz, 2H), 4.20 (s, 1H), 4.29 (t, J=1.63 Hz, 2H), 7.05-7.50 (m, 9H).

Example 10

(R,S)-4-{4-[(4-fluorophenyl)phenylmethyl]piperazin-1-yl}but-2-yn-1-ol (by method B in Example 10), (Xc, X=F; X'=Y=Y'=R1=R2=H; m=1)

A solution of methanesulfonyl chloride (1.86 g, 16.27 mmol) and tetrahydrofuran (5 ml) is added dropwise to a stirred solution of 2-butyne-1,4-diol (3.82 g, 44.3 mmol) and diisopropylethylamine (6.30 g, 48.8 mmol) in tetrahydrofuran (20 ml) during 30 min at 0-5° C. After 1 hr stirring the temperature is raised to 25-30° C. and stirred for further 1 hr. The resulting mixture containing mesylate of 2-butyne-1,4-diol is added dropwise to a stirred solution of (R,S)-1-[(4-fluorophenyl)phenylmethyl]piperazine (4.0 g, 14.79 mol) in tetrahydrofuran (25 ml) during 1 hr at 5-10° C. The reaction mass is stirred at 5-10° C. for 1 hr and then at 25-30° C. for further 5 hrs. Thereafter, citric acid (3.2 g, 0.01523 mol) is added and the mixture is concentrated under reduced pressure at below 60° C. to remove most of the solvent. Water (50 ml) is charged to the residual mass and the resulting aqueous layer washed with hexane (2×30 ml), basified to pH=9-10 and the product extracted into dichloromethane (3×30 ml). The dichloromethane layer is washed with water (25 ml) and degassed to obtain crude product as a sticky solid, which is purified by flash column chromatography on silica gel using dichloromethane-methanol (9.2:0.8) as mobile phase to obtain pure product as a thick syrupy mass.

$^1$H-NMR (CDCl$_3$, δppm): 1.87 (b), 2.25-2.70 (m, 8H), 3.30 (t, J=1.83 Hz, 2H), 4.2.1 (s, 1H), 4.29 (t, J=1.78 Hz, 2H), 6.85-7.02 (m, 2H), 7.13-7.42 (m, 7H).

Example 11

4-{4-[Bis-(4-fluorophenyl)methyl]piperazin-1-yl)-(E)-but-2-en-1-ol, (XIVa, X=X'=4-F; Y=Y'=R1=R2=R3=R4=H; m=n=1)

To a stirred solution of methyl 4-{4-[bis-(4-fluorophenyl)methyl]piperazin-1-yl}-(E)-but-2-enoate (380 g, 0.984 mol) in tetrahydrofuran (1900 ml) at −10 to 0° C. is added dropwise DIBALH (560 g, 3.938 mol, as 20% solution in toluene) during about 2-3 hrs. After completion of addition, the reaction mass is stirred for further 1.0 hrs at 0 to 10° C. and then quenched by sequential addition of ethyl acetate (400 ml) and water (800 ml). After vigorous stirring for 2 hrs the mass is filtered. The organic layer is separated from the filtrate, washed with water (1500 ml) and concentrated to get crude product.

The crude product is taken in toluene (2000 ml), extracted into 10% acetic acid (2000 ml), the aqueous extract basified to pH 9-10 with 20% aqueous sodium hydroxide and the product extracted into dichloromethane (3×1500 ml). The dichloromethane layer is washed with water (800 ml) and concentrated to get a syrupy mass which is purified by flash column chromatography on silica gel using toluene-methanol (9:1) as mobile phase.

$^1$H-NMR (CDCl$_3$, δppm): 1.70 (br, D$_2$O exchangeable), 2.20-2.70 (m, 8H), 3.00 (d, J=5.38 Hz, 2H), 4.12 (d, J=4.40 Hz, 2H), 4.21 (s, 1H), 5.65-5.90 (m, 2H), 6.85-7.05 (m, 4H), 7.28-7.40 (m, 4H).

Example 12

4-{4-[Bis-(4-fluorophenyl)methyl]piperazin-1-yl}-(E)-but-2-en-1-ol (XIa, X=X'=4-F; Y=Y'=R1=R2=H; m=1)

To a stirred solution of 4-{4-[bis-(4-fluorophenyl)methyl]piperazin-1-yl}but-2-yn-1-ol (135 g, 0.379 mol) in tetrahydrofuran (4300 ml) at 5-10° C. is added lithium aluminum hydride (43.1 g, 1.136 mol) in portions during 34 hrs. The reaction mixture is stirred for further 5-6 hrs. and then quenched by addition of ethyl acetate (135 ml), followed by water (100 ml) at 5-10° C. The resulting mixture is filtered, the organic layer separated from the filtrate, and concentrated to get crude product, which is purified by flash column chromatography on silica gel using toluene-methanol (9:1) as mobile phase to obtain pure product.

$^1$H-NMR (CDCl$_3$, δppm): 1.77 (br, D$_2$O exchangeable), 2.20-2.70 (m, 8H), 3.00 (d, J=4.91 Hz, 2H), 4.11 (d, J=3.71 Hz, 2H), 4.21 (s, 1H), 5.55-5.90 (m, 2H), 6.80-7.05 (m, 4H), 7.10-7.50 (m, 4H).

Example 13

(R,S)-4-{14[(4-chlorophenyl)phenylmethyl]piperazin-1-yl}-(E)-but-2-en-1-ol, (XIb, X=Cl; X'=Y=Y'=R1=R2=H; m=1)

(R,S)-4-{4-[(4-chlorophenyl)phenylmethyl]piperazin-1-yl}but-2-yn-1-ol (3.5 g, mol) is converted to (R,S)-4-{4-[(4-chlorophenyl)phenylmethyl]piperazin-1-yl)-(E)-but-2-en-1-ol in a manner similar to example 14. Crude product is obtained as a syrupy mass, which is purified by flash column chromatography on silica gel using toluene-methanol (9:1) as mobile phase to obtain pure product.

$^1$H-NMR (CDCl$_3$, δppm): 2.20-2.65 (m, 8H), 3.00 (d, J=4.83 Hz, 2H), 4.11 (d, J=3.52 Hz, 2H), 4.20 (s, 1H), 5.60-5.90 (m, 2H), 7.00-7.50 (m, 9H).

Example 14

(R,S)-4-{4-[(4-fluorophenyl)phenylmethyl]piperazin-1-yl}-(E)-but-2-en-1-ol (XIc, X=F; X'=Y=Y'=R1=R2=H; m=1)

(R,S)-4-{4-[(4-fluorophenyl)phenylmethyl]piperazin-1-yl}but-2-yn-1-ol (2.13 g, 0.0063 mol) is converted to (R,S)-4-(4-[(4-fluorophenyl)phenylmethyl]piperazin-1-yl}-(E)-but-2-en-1-ol in a manner similar to example 14. Crude product obtained is obtained as a syrupy mass which is purified by flash column chromatography on silica gel using dichloromethane-methanol (9.3:0.7) as mobile phase to obtain pure product.

$^1$H-NMR (CDCl$_3$, δppm): 1.71 (br, exchangeable by D$_2$O), 2.10-2.70 (m, 8H), 3.00 (d, J=5.23 Hz, 2H), 4.11 (d, J=4.20 Hz, 211), 4.22 (s, 2H), 5.65-5.90 (m, 2H), 6.85-7.02 (m, 2H), 7.10-7.45 (m, 7H).

Example 15

Methyl 4-{4-[Bis-(4-fluorophenyl)methyl]piperazin-1-yl}-(E)-but-2-enoate, (XIIIa, X=X'=4-F; R=CH$_3$; Y=Y'=R1=R2=R3=R4=H; m=n=1)

A solution of methyl-4-bromocrotonate (46.56 g, 0.260 mol) in toluene (50 ml) is added dropwise to a mixture containing 1-[bis-(4-fluorophenyl)methyl]piperazine (50 g, 0.173 mol), diisopropylethylamine (49.30 g, 0.381 mol) in toluene (250 ml) at 25-30° C. during 30 minutes. After stirring for 8 hrs, the reaction mass is washed successively with water (2×150 ml), 0.2N hydrochloric acid (3×150 ml), and water (150 ml). To the organic layer at 5-10° C. is added 3N hydrochloric acid (200 ml), stirred and the aqueous layer containing product is separated. It is then washed with toluene (200 ml), basified to pH=9-10 with 20% sodium hydroxide solution and the product extracted into ethyl acetate (2×150 ml). The organic layer is washed once with water (100 ml), concentrated and degassed. The residue is triturated with hexane (150 ml) and the solid filtered. The product is further purified by recrystallization from cyclohexane.

$^1$H-NMR (CDCl$_3$, δppm): 1.63 (br, 1H, D$_2$O exchangeable), 2.20-2.65 (m, 8H), 3.13 (d, J=5.00 Hz, 2H), 3.72 (s, 3H), 4.22 (s, 1H), 5.88-6.03 (m, 1H), 6.80-7.05 (m, 5H), 7.20-7.40 (m, 4H).

Example 16

Methyl 4-{4-[(4-chlorophenyl)phenylmethyl]piperazin-1-yl}-(E)-but-2-enoate, (XIIIb, X=Cl; X'=Y=Y'=R1=R2=R3=R4=H; m=n=1)

A solution containing (R,S)-1-[(4-chlorophenyl)phenylmethyl]piperazine (5 g, 0.0174 mol), DMF (30 ml), methyl-4-bromocrotonate (4.7 g, 0.0263 mol), and diisopropylethylamine (6.75 g, 0.0522 mol) is stirred at 27-30° C. for 6 hrs. The reaction is quenched with water (40 ml) and the product extracted into dichloromethane (3×30 ml). The organic layer is washed with water (2×30 ml) and concentrated to obtain crude product which is purified by flash column chromatography on silica gel using ethyl acetate-hexane (6.5:3.5) as mobile phase to obtain pure product.

$^1$H-NMR (CDCl$_3$, δppm): 2.20-2.65 (m, 8H), 3.14 (dd, J$_1$=6.20 Hz, J$_2$=1.39 Hz, 2H), 3.72 (s, 3H), 4.20 (s, 1H), 5.85-6.05 (m, 1H), 6.8-7.05 (m, 1H), 7.05-7.50 (m, 9H).

Example 17

{4-{4-[Bis-(4-fluorophenyl)methyl]-piperazin-1-yl)-(Z)-but-2-enyloxy}acetic acid dihydrochloride, (Ia)

To a stirred solution of 4-{4-[bis-(4-fluorophenyl)methyl]piperazin-1-yl}-(Z)-but-2-en-1-ol (97.0 g, 0.271 mol) and potassium tert-butoxide (54.7 g, 0.487 mol) in anhydrous tert-butanol (776 ml), preheated at 60-65° C. for 1 hr., under nitrogen atmosphere, is added dry sodium chloroacetate (63 g, 0.541 mol). The reaction mass is then refluxed for further 5 hrs. The mixture is then concentrated under reduced pressure at below 60° C. until tert-butanol is completely removed. The residue is taken up in water (800 ml) and washed with ethyl acetate (2×500 ml). The aqueous solution is then acidified to pH 5-6, extracted into dichloromethane (3×500 ml), washed dichloromethane layer with water (300 ml), and concentrated to get crude product, which is purified by flash column chromatography on silica gel using toluene-methanol (4:1) as mobile phase to obtain pure product.

$^1$H-NMR (CDCl$_3$, δppm): 2.40-2.80 (m, 4H), 2.80-3.20 (m, 4H), 3.65 (d, J=7.51 Hz, 2H), 3.96 (s, 2H), 4.19 (d, J=4.51 Hz, 2), 4.32 (s, 1H), 5.00-5.30 (m, 1H), 5.30-6.10 (m, 1H), 6.80-7.05 (m, 4H), 7.00-7.50 (m, 4H)

A suspension of {4-[4-[bis-(4-fluorophenyl)methyl]piperazin-1-yl]-(Z)-but-2-enyloxy}acetic acid (83.8 g, 0.201 mol) and water (335 ml) is acidified under stirring to pH 1-2 with 6N hydrochloric acid at 25-30° C. The solution is filtered, concentrated under reduced pressure at below 50° C. (until volume of solution is around 170 ml), and lyophilized to obtain the dihydrochloride salt.

Example 18

(R,S)-4-[4-[(4-Chlorophenyl)phenylmethyl]piperazin-1-yl]-(Z)-but-2-enyloxy}acetic acid dihydrochloride, [Ib (R,S)]

(R,S)-4-{4-[(4-chlorophenyl)phenylmethyl]piperazin-1-yl}-(Z)-but-2-en-1-ol (100.0 g, 0.28 mol) is converted to (R,S)-{4-[4-[(4-chlorophenyl)phenylmethyl]piperazin-1-yl]-(Z)-but-2-enyloxy}acetic acid in a manner similar to example 19. Crude product is obtained is as a foamy solid which is purified by flash column chromatography on silica gel using toluene-methanol (4:1) as mobile phase to obtain pure product.

$^1$H-NMR (CDCl$_3$, δppm): 2.40-2.75 (m, 4H), 2.75-3.20 (m, 4H), 3.62 (d, J=7.43 Hz, 2H), 3.95 (s, 2H), 4.17 (d, 3=4.9 Hz, 2H), 4.28 (s, 1H), 5.50-5.80 (m, 1H), 5.80-6.1 (m, 1H), 6.95-7.40 (m, 9H), 8.98 (br, exchangeable with D$_2$O)

It was converted to dihydrochloride salt as per example 17.

Example 19

[4-(4-Benzhydrylpiperazin-1-yo)-(Z)-but-2-enyloxy] acetic acid dihydrochloride, (Ic)

4-(4-Benzhydrylpiperazin-1-yl)-(Z)-but-2-en-1-ol (2.1 g, 0.0065 mol) is converted to [4-(4-benzhydrylpiperazin-1-yl)-(Z)-but-2-enyloxy]acetic acid in a manner similar to example 17. The crude product obtained as a foamy solid is purified by flash column chromatography on silica gel using toluene-methanol (8.5:1.5) as mobile phase to obtain pure product.

$^1$H-NMR (CDCl$_3$, δppm): 2.40-2.85 (m, 4H), 2.85-3.20 (m, 4H), 3.68 (d, J=7.53 Hz, 2H), 3.96 (s, 2H), 4.18 (d, J=4.60 Hz, 2H), 4.33 (s, 1H), 5.50-5.80 (m, 1H), 5.90-6.10 (m, 1H), 7.00-7.50 (m, 10H)

It is converted to dihydrochloride salt as per example 19.

Example 20

{4-[Bis-(2,4-difluorophenyl)methyl]-piperazin-1-yl}-(Z)-but-2-enyloxy}acetic Acid Dihydrochloride, (Id)

4-{4-[Bis-(2,4-difluorophenyl)methyl]piperazin-1-yl}-(Z)-but-2-en-1-ol (6.2 g, 0.0157 mol) is converted {4-{4-[bis-(2,4-difluorophenyl)methyl]-piperazin-1-yl}-(Z)-but-2-enyloxy}acetic acid in a manner similar to example 17. Crude product is obtained is as a foamy solid which is purified by flash column chromatography on silica gel using toluene-methanol (4:1) as mobile phase to obtain pure product.

¹H-NMR (CDCl₃, δppm): 2.20-2.75 (m, 4H), 2.75-3.20 (m, 4H), 3.57 (d, J=6.07 Hz, 2H), 3.96 (s, 2H), 4.17 (d, J=3.90 Hz, 2H), 4.99 (s, 1H), 5.50-6.10 (m, 2H), 6.45-7.0 (m, 4H), 7.20-7.65 (m, 2H), 9.87 (br)

The product is taken up in ethyl acetate (12 ml), acidified with a solution of anhydrous HCl in ethyl acetate to pH 1.0 to 2.0, concentrated and degassed to get the dihydrochloride salt.

Example 21

{4-[4-[Bis-(4-chlorophenyl)methyl]-piperazin-1-yl]-(Z)-but-2-enyloxy}acetic acid dihydrochloride, (Ie)

4-{4-[Bis-(4-chlorophenyl)methyl]piperazin-1-yl}-(Z)-but-2-en-1-ol (2.26 g, mol) is converted to {4-[4-[bis-(4-chlorophenyl)methyl]-piperazin-1-yl]-(Z)-but-2-enyloxy}acetic acid in a manner similar to example 17. Crude product obtained is purified by flash column chromatography on silica gel using toluene-methanol (4:1) as mobile phase to obtain pure product.

¹H-NMR (CDCl₃, δppm): 2.50-2.80 (m, 4H), 2.80-3.20 (m, 4H), 3.60 (d, J=7.38 Hz, 2H), 3.94 (s, 2H), 4.20 (d, J=4.08 Hz, 2H), 4.31 (s, 1H), 5.23 (br, exchangeable with D₂O), 5.50-5.80 (m, 1H), 5.80-6.10 (m, 1H), 7.10-7.40 (m, 8H).

The product was converted to dihydrochloride salt as in example 17.

Example 22

{c4-{4-[Bis-(4-fluorophenyl)methyl]-piperazin-1-yl}-(Z)-but-2-enyloxy}acetic acid methyl ester dihydrochloride, (If)

To a stirred solution of {4-{4-[bis-(4-fluorophenyl)methyl]-piperazin-1-yl}-(Z)-but-2-enyloxy}acetic acid (35 g, 0.084 mol) in methanol (560 ml), is added a solution of anhydrous HCl in ethyl acetate till pH is 1-2. The solution is refluxed for 2 hrs, cooled to 25-30° C. and stirred for 4 hrs. The crystallized solid is filtered, washed with ethyl acetate (2×5 ml), and dried in oven at 60-65° C. to get the product.

¹H-NMR (D₂O, δppm): 3.20-3.60 (m, 8H), 3.64 (s, 3H), 3.94 (d, J=7.66 Hz, 2H), 4.00-4.20 (m, 4H), 5.31 (s, 1H), 5.50-5.78 (m, 1H), 5.90-6.20 (m, 1H), 6.85-7.15 (m, 4H), 7.30-7.60 (m, 4H).

Example 23

{4-{4-[Bis-(4-fluorophenyl)methyl]-piperazin-1-yl}-(Z)-but-2-enyloxy}acetic acid ethyl ester dihydrochloride, (Ig)

To a stirred solution of {4-{4-[bis-(4-fluorophenyl)methyl]-piperazin-1-yl}-(Z)-but-2-enyloxy}acetic acid (1.0 g, 0.0024 mol) in ethanol (20 ml), is added a solution of anhydrous ethanolic HCl till pH is 1-2. The solution is refluxed for around 2 hrs, cooled to 25-30° C. and stirred for 4 hrs. The crystallized solid is filtered, washed with ethanol (2×5 ml), and dried in oven at 60-65° C. to get the product.

¹H-NMR (CDCl₃+DMSO-d₆, δppm): 1.28 (t, J=7.10 Hz, 3H), 2.70-4.30 (m, 17H), 5.70-6.20 (m, 2H), 7.10 (t, J=8.62 Hz, 4H), 7.40-7.80 (m, 4H).

Example 24

{4-{4-[Bis-(4-fluorophenyl)methyl]-piperazin-1-yl}-(Z)-but-2-enyloxy}acetic acid isopropyl ester dihydrochloride, (Ih)

To a stirred solution of {4-{4-[bis-(4-fluorophenyl)methyl]piperazin-1-yl}-(Z)-but-2-enyloxy}acetic acid (1.0 g, 0.0024 mol) in isopropyl alcohol (20 ml), is added a solution of anhydrous HCl in isopropyl alcohol till pH of solution is 1-2. The solution is refluxed for around 2 hrs, cooled to 25-30° C. and stirred for 4 hrs. The crystallized solid is filtered, washed with isopropyl alcohol (2×5 ml), and dried in oven at 60-65° C. to get product 0.968 g (75.85% yield).

¹H-NMR (CDCl₃+DMSO-d₆, δppm): 1.23 (d, J=6.25 Hz, 6H), 2.60-3.70 (m, 8H), 3.70-4.40 (m, 7H), 4.80-5.20 (m, 1H), 5.60-5.90 (m, 1H), 5.90-6.10 (m, 1H), 7.16 (t, J=8.56 Hz, 4H), 7.40-7.90 (m, 4H).

Example 25

(R,S)-{4-14[(4-chlorophenyl)phenylmethyl]piperazin-1-yl]-(Z)-but-2-enyloxy}acetic Acid Isopropyl Ester Dihydrochloride, (Ii):

The preparation was carried out using (R,S)-{4-[4-[(4-chlorophenyl)phenylmethyl]piperazin-1-yl]-(Z)-but-2-enyloxy}acetic acid in a manner similar to example 24.

¹H-NMR (CDCl₃+DMSO-d₆, δppm): 1.26 (d, J=6.26 Hz, 6H), 2.80-3.70 (m, 8H), 3.80-4.15 (m, 3H), 4.21 (d, J=5.57 Hz, 4H), 4.90-5.15 (m, 1H), 5.70-5.95 (m, 1H), 5.95-6.15 (m, 1H), 7.10-7.90 (m, 9H).

Example 26

(R,S)-{4-[4-[(4-chlorophenyl)phenylmethyl]piperazin-1-yl]-(Z)-but-2-enyloxy}acetic acid methyl ester dihydrochloride, (Ij)

To a stirred solution of (R,S)-{4-[4-[(4-chlorophenyl)phenylmethyl]piperazin-1-yl]-(Z)-but-2-enyloxy}acetic acid (1 g, 0.0024 mol) in methanol (20 ml), is added a solution of anhydrous HCl in ethyl acetate till pH of the solution is 1-2. The solution is refluxed for 2 hrs, cooled to 25-30° C., added anhydrous diethyl ether till slight haziness and stirred for 4 hrs. The crystallized solid is filtered, washed with diethyl ether (2×5 ml), and dried in oven at 60-65° C. to get product.

¹H-NMR (CDCl₃+DMSO-d₆, δppm): 3.10-3.90 (m, 8H), 3.73 (s, 3H), 3.90-4.30 (m, 7H), 5.70-6.00 (m, 1H), 6.00-6.20 (m, 1H), 7.10-7.50 (m, 5H), 7.50-8.00 (m, 4H).

Example 27

(R,S)-{4-[4-[(4-chlorophenyl)phenylmethyl]piperazin-1-yl]-(Z)-but-2-enyloxy}acetic Acid Ethyl Ester Dihydrochloride, (Ik)

The preparation was carried out using (R,S)-{4-[4-[(4 chlorophenyl)phenylmethyl]piperazin-1-yl]-(Z)-but-2-enyloxy}acetic acid in a manner similar to example 25, to obtain the product.

¹H-NMR (CDCl₃+DMSO-d₆, δppm): 1.27 (t, J=7.12 Hz, 3H), 3.10-3.90 (m, 8H), 3.90-4.30 (m, 9H), 5.75-5.95 (m, 1H), 5.95-6.15 (m, 1H), 7.10-7.50 (m, 5H), 7.50-8.00 (m, 4H).

Example 28

{2-{4-[bis-(4-fluorophenyl)methyl]piperazin-1-ylmethyl}benzyloxy}acetic acid dihydrochloride, (IIa)

{2-{4-[Bis-(4-fluorophenyl)methyl]piperazin-1-ylmethyl}phenyl}methanol (5.0 g, 0.0122 mol) is converted to {2-{4-[Bis-(4-fluorophenyl)methyl]piperazin-1-ylmethyl}benzyloxy}acetic acid in a manner similar to example 17. Crude product obtained is purified by flash column chromatography on silica gel using toluene-methanol (8.5:1.5) as mobile phase to obtain pure product as a white foamy solid.

$^1$H-NMR (CDCl$_3$, δppm): 2.40-2.75 (m, 4H), 2.75-3.20 (m, 4H), 4.06 (s, 2H), 4.10 (s, 2H), 4.28 (s, 1H), 4.58 (s, 2H), 6.70-7.10 (m, 4H), 7.10-7.50 (m, 8H).

The product is taken up in ethyl acetate (12 ml), acidified with a solution of anhydrous HCl in ethyl acetate to pH 1.0 to 2.0, concentrated and degassed to get dihydrochloride salt as a white solid.

Example 29

(R,S) {2-{4-[(4-chlorophenyl)phenylmethyl]piperazin-1-ylmethyl}benzyloxy}acetic acid dihydrochloride, (IIb)

{2-{4-[(4-chlorophenyl)phenylmethyl]piperazin-1-ylmethyl}phenyl}methanol (4.0 g, 9.83 mmol) is converted to {2-{4-[(4-chlorophenyl)phenylmethyl]piperazin-1-ylmethyl}benzyloxy}acetic acid in a manner similar to example 17. Crude product obtained as an off-white foamy solid is purified by flash column chromatography on silica gel using toluene-methanol (8.5:1.5) as mobile phase to obtain pure product as a white foamy solid.

$^1$H-NMR (CDCl$_3$, δppm): 2.40-2.80 (m, 4H), 2.80-3.20 (m, 4H), 4.06 (s, 2H), 4.14 (s, 2H), 4.28 (s, 1H), 4.58 (s, 2H), 7.00-7.50 (m, 13H).

The product is converted to dihydrochloride salt using a solution of anhydrous HCl in ethyl acetate as in example 28.

Example 30

{4-[4-[Bis-(4-fluorophenyl)methyl]piperazin-1-yl]-(E)-but-2-enyloxy}acetic acid dihydrochloride, (IIIa)

To a stirred solution of 4-{4-[bis-(4-fluorophenyl)methyl]piperazin-1-yl}-(E)-but-2-en-1-ol (247.0 g, 0.689 mol) and potassium tert-butoxide (139.2 g, 1.240 mol) in anhydrous tert-butanol (2000 ml), preheated at 60-65° C. for 1 hr. under nitrogen atmosphere, is added dry sodium chloroacetate (160.5 g, 1.378 mol). The reaction mass is then refluxed for further 5 hrs. The mixture is then concentrated under reduced pressure at below 60° C. until tert-butanol is completely removed. The residue is taken up in water (1500 ml) and washed with ethyl acetate (2×1500 ml). The aqueous solution is then acidified to pH 5-6, extracted into dichloromethane (2×750 ml), washed dichloromethane layer with water (300 ml), and concentrated to get crude product as a foamy solid. The crude product is purified by flash column chromatography on silica gel using toluene-methanol (4:1) as mobile phase. The product was converted to its dihydrochloride salt as in example 17.

$^1$H-NMR (D$_2$O, δppm): 3.20-3.70 (m, 8H), 3.82 (d, J=6.79 Hz, 2H), 3.93-4.05 (m, 4H), 5.35 (s, 1H), 5.65-5.80 (m, 1H), 5.97-6.12 (m, 1H), 6.80-7.00 (m, 4H), 7.36-7.50 (m, 4H).

Example 31

(R,S)-{4-[4-[(4-Chlorophenyl)phenylmethyl]piperazin-1-yl]-(E)-but-2-enyloxy}acetic acid dihydrochloride, (IIIb)

(R,S)-4-{4-[(4-Chlorophenyl)phenylmethyl]piperazin-1-yl}-(E)-but-2-en-1-ol (1.9 g, 0.0053 mol) is converted to (R,S)-{4-[4-[(4-Chlorophenyl)phenylmethyl]piperazin-1-yl]-(E)-but-2-enyloxy}acetic acid as in example 30. Crude product is obtained as a foamy solid which is purified by flash column chromatography on silica gel using toluene-methanol (8:2) as mobile phase to obtain pure product.

$^1$H-NMR (CDCl$_3$, δppm): 2.40-2.75 (m, 4H), 2.75-3.20 (m, 4H), 3.30-3.50 (m, 2H), 3.93 (s, 2H), 4.00-4.15 (m, 2H), 4.26 (s, 1H), 5.70-6.00 (m, 21), 6.82 (br), 7.00-7.50 (m, 9H)

It was converted to dihydrochloride salt as per example 17.

Example 32

(R,S)-{4-[4-[(4-fluorophenyl)phenylmethyl]piperazin-1-yl]-(E)-but-2-enyloxy}acetic acid dihydrochloride, (IIIc)

(R,S)-4-{4-[(4-Fluorophenyl)phenylmethyl]piperazin-1-yl}-(E)-but-2-en-1-ol (0.7 g, 2.06 mmol) is converted to (R,S)-{4-[4-[(4-fluorophenyl)phenylmethyl]piperizin-1-yl]-(E)-but-2-enyloxy}acetic acid as per example 30. The crude product obtained (0.77 g) is purified by flash column chromatography on silica gel using toluene-methanol (3:2) as mobile phase to obtain pure product.

$^1$H-NMR (CDCl$_3$, δppm): 2.40-3.20 (m, 8H), 3.20-3.50 (m, 2H), 3.92 (s, 2H), 4.00-4.15 (m, 2H), 4.26 (s, 1H), 5.65-5.95 (m, 2H), 6.80-7.03 (m, 2H), 7.07-7.50 (m, 7H), 10.70 (br, exchangeable).

It is converted to its dihydrochloride salt as in example 17.

IC$_{50}$ Determination Using Isolated Guinea Pig Ileum Functional Assay

Terminal segment of ileum of junction of Dunken Hartley guinea pig, of about 10 cm from the ileo-caecal, separated from mesenteric attachments was immediately removed and placed in Tyrode solution of composition, NaCl 137.0 mM, KCl 2.7 mM, CaCl$_2$ 1.8 mM, MgCl$_2$ 1.05 mM, NaHCO$_3$ 11.9 mM, NaH$_2$PO$_4$ 0.42 mM and glucose 5.6 mM, maintained at 35° C.

The lumen of the ileum was gently cleaned with Tyrode so as to remove any particle without affecting the mucosal layer of the tissue. Pieces of 1.5-2.0 cm length were cut and placed in the organ bath of 20 ml capacity, attaching one end to the tissue holder and other to the transducer by a fine cotton thread. The system was previously calibrated before start of each experiment. Tissue was kept under a resting tension of 0.5-0.75 g. The bath solution was continuously bubbled with 95% O$_2$ and 5% CO$_2$ and maintained at 35° C. temperature. After an initial 30 min of equilibration time the baseline was recorded and non-cumulative responses with sub maximal dose of histamine (7.2×10$^{-7}$M) were initially recorded until the responses were reproducible. The contractions to this typical dose of histamine in absence (only vehicle) and presence of at least 3 different concentrations of the test compounds were recorded after 15 min constant incubation time. The percentage inhibitions caused by different concentrations of test compounds were plotted against the log of molar concentrations of the test compounds for the determination of $IC_{50}$.

6; with a proviso that when $R_3$ & $R_4$ together do not form part of a ring they may exist in either E or Z configuration; $R_5$ is $(CH_2)_n$—O—$CH_2$—CO-Z wherein n is 1 to 6; Z is selected from OH, OR, NRR',
N(OR)R', N(R)-N(R)R' and

TABLE-1

The compound of formula I is tested for its activity in its hydrochloride salt form

| Compd. | X | Y | X' | Y' | $R_1$ | $R_2$ | $R_3$ | $R_4$ | m | n | Z | $IC_{50}$ (mean) ± SEM (moles) |
|---|---|---|---|---|---|---|---|---|---|---|---|---|
| Ia | 4-F | H | 4-F | H | H | H | H | H | 1 | 1 | OH | $2.17 \times 10^{-6} \pm 4.23 \times 10^{-7}$ |
| Ib | 4-Cl | H | H | H | H | H | H | H | 1 | 1 | OH | $2.13 \times 10^{-7} \pm 5.37 \times 10^{-8}$ |
| Ic | H | H | H | H | H | H | H | H | 1 | 1 | OH | $1.30 \times 10^{-6} \pm 4.17 \times 10^{-7}$ |
| Id | 2-F | 4-F | 2-F | 4-F | H | H | H | H | 1 | 1 | OH | $2.26 \times 10^{-6} \pm 5.37 \times 10^{-7}$ |
| Ie | 4-Cl | H | 4-Cl | H | H | H | H | H | 1 | 1 | OH | $3.27 \times 10^{-7} \pm 3.59 \times 10^{-7}$ |
| If | 4-F | H | 4-F | H | H | H | H | H | 1 | 1 | $OCH_3$ | $4.00 \times 10^{-7} \pm 2.91 \times 10^{-7}$ |
| Ig | 4-F | H | 4-F | H | H | H | H | H | 1 | 1 | $OC_2H_5$ | $4.09 \times 10^{-7} \pm 3.39 \times 10^{-8}$ |
| Ih | 4-F | H | 4-F | H | H | H | H | H | 1 | 1 | $O^{iso}Pr$ | $4.66 \times 10^{-7} \pm 1.20 \times 10^{-8}$ |
| Ii | 4-Cl | H | H | H | H | H | H | H | 1 | 1 | $O^{iso}Pr$ | $2.37 \times 10^{-7} \pm 3.54 \times 10^{-9}$ |
| Ij | 4-Cl | H | H | H | H | H | H | H | 1 | 1 | $OCH_3$ | $4.66 \times 10^{-7} \pm 3.54 \times 10^{-8}$ |
| Ik | 4-Cl | H | H | H | H | H | H | H | 1 | 1 | $OC_2H_5$ | $7.35 \times 10^{-7} \pm 1.85 \times 10^{-7}$ |
| IIa | 4-F | H | 4-F | H | H | H | Part of benzene ring | | 1 | 1 | OH | $1.19 \times 10^{-6} \pm 7.01 \times 10^{-7}$ |
| IIb | 4-Cl | H | H | H | H | H | Part of benzene ring | | 1 | 1 | OH | $5.64 \times 10^{-7} \pm 1.91 \times 10^{-3}$ |
| IIIa | 4-F | H | 4-F | H | H | H | H | H | 1 | 1 | OH | $4.72 \times 10^{-6} \pm 5.90 \times 10^{-6}$ |
| IIIb | 4-Cl | H | H | H | H | H | H | H | 1 | 1 | OH | $3.93 \times 10^{-7} \pm 1.84 \times 10^{-7}$ |
| IIIc | 4-F | H | H | H | H | H | H | H | 1 | 1 | OH | $8.77 \times 10^{-7} \pm 5.13 \times 10^{-7}$ |
| Cetirizine | | | | | | | | | | | | $3.16 \times 10^{-6} \pm 4.09 \times 10^{-6}$ |

We claim:

1. A compound of formula I

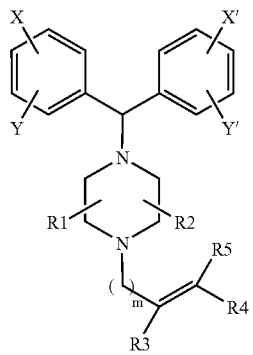

Formula I

wherein X, Y, X' & Y' are selected from hydrogen, halogen, substituted or unsubstituted alkyl (linear, branched or cyclo), aryl, alkyloxy and haloalkyl group; $R_1$, $R_2$, $R_3$ & $R_4$ are selected from hydrogen, substituted or unsubstituted alkyl groups (linear, branched or cyclo), aryl, heteroaryl groups or aralkyl groups, heterocycles containing one or more of hetero atoms (viz., N, S, O), substituted or unsubstituted alkenyl or alkynyl groups of carbon 2 to 6; wherein the substituents $R_1$ & $R_2$ on the piperazinyl moiety are either syn or anti to each other and optionally $R_3$ and $R_4$ together with the carbons to which they are attached form a monocyclic saturated or aryl or substituted aryl or heteroaryl or substituted heteroaryl ring containing one or more hetero atoms selected from N, S and O with a ring size ranging from 3 to 6; with a proviso that when $R_3$ & $R_4$ together do not form part of a ring they may exist in either E or Z configuration; $R_5$ is $(CH_2)_n$—O—$CH_2$—CO-Z wherein n is 1 to 6; Z is selected from OH, OR, NRR',
N(OR)R', N(R)-N(R)R' and wherein R & R' are selected from hydrogen, substituted or unsubstituted alkyl groups (linear, branched or cyclo), aryl, heteroaryl groups or aralkyl groups, heterocycles containing one or more of hetero atoms (viz., N, S, O), substituted or unsubstituted alkenyl or alkynyl groups of carbon 2 to 6; and B is selected from —(CH2)n- (n is 1 to 6) and —(CH2)x-D—(CH2)y where D is O, NR, S or SO2, x and y are independently 1 to 6; and m is selected from 1 to 6; and pharmaceutically acceptable salts thereof.

2. A compound as claimed in claim 1 wherein X, Y, X' & Y' are selected from hydrogen, chloro and fluoro;

$R_1$ and $R_2$, are hydrogen;

$R_3$ and $R_4$ are hydrogen existing in the E or Z configuration or optionally when they are in Z-configuration $R_3$ and $R_4$ together with the carbons to which they are attached form a benzene ring; and $R_5$ is $CH_2$—O—$CH_2$—CO-Z wherein Z is selected from OH and OR wherein R may be selected from methyl, ethyl and isopropyl;

and m is 1.

3. A compound of claim 1, which is {4-{4-[Bis-(4-fluorophenyl)methyl]-piperazin-1-yl}-(Z)-but-2-enyloxy}acetic acid or its pharmaceutically acceptable salt.

4. A compound of claim 1, which is {4-[4-[(4-Chlorophenyl)phenylmethyl]piperazin-1-yl]-(Z)-but-2-enyloxy}acetic acid or its pharmaceutically acceptable salt.

5. A compound of claim 1, which is [4-(4-Benzhydrylpiperazin-1-yl)-(Z)-but-2-enyloxy]acetic acid or its pharmaceutically acceptable salt.

6. A compound of claim 1, which is {4-{4-[Bis-(2,4-difluorophenyl)methyl]-piperazin-1-yl}-(Z)-but-2-enyloxy}acetic acid or its pharmaceutically acceptable salt.

7. A compound of claim 1, which is {4-[4-[Bis-(4-chlorophenyl)methyl]-piperazin-1-yl]-(Z)-but-2-enyloxy}acetic acid or its pharmaceutically acceptable salt.

8. A compound of claim 1, which is {4-{4-[Bis-(4-fluorophenyl)methyl]-piperazin-1-yl}-(Z)-but-2-enyloxy}acetic acid methyl ester or its pharmaceutically acceptable salt.

9. A compound of claim 1, which is {4-{4-[Bis-(4-fluorophenyl)methyl]-piperazin-1-yl}-(Z)-but-2-enyloxy}acetic acid ethyl ester or its pharmaceutically acceptable salt.

10. A compound of claim 1, which is {4-{4-[Bis-(4-fluorophenyl)methyl]-piperazin-1-yl}-(Z)-but-2-enyloxy}acetic acid isopropyl ester or its pharmaceutically acceptable salt.

11. A compound of claim 1, which is {4-[4-[(4-chlorophenyl)phenylmethyl]piperazin-1-yl]-(Z)-but-2-enyloxy}acetic acid isopropyl ester or its pharmaceutically acceptable salt.

12. A compound of claim 1, which is {4-[4-[(4-chlorophenyl)phenylmethyl]piperazin-1-yl]-(Z)-but-2-enyloxy}acetic acid methyl ester or its pharmaceutically acceptable salt.

13. A compound of claim 1, which is {4-[4-[(4-chlorophenyl)phenylmethyl]piperazin-1-yl]-(Z)-but-2-enyloxy}acetic acid ethyl ester or its pharmaceutically acceptable salt.

14. A compound of claim 1, which is {2-{4-[Bis-(4-fluorophenyl)methyl]piperazin-1-ylmethyl}benzyloxy}acetic acid or its pharmaceutically acceptable salt.

15. A compound of claim 1, which is {2-{4-[(4-Chlorophenyl)phenylmethyl]piperazin-1-ylmethyl}benzyloxy}acetic acid or its pharmaceutically acceptable salt.

16. A compound of claim 1, which is {4-[4-[Bis-(4-fluorophenyl)methyl]piperizin-1-yl]-(E)-but-2-enyloxy}acetic acid or its pharmaceutically acceptable salt.

17. A compound of claim 1, which is {4-[4-[(4-Chlorophenyl)phenylmethyl]piperizin-1-yl]-(E)-but-2-enyloxy}acetic acid or its pharmaceutically acceptable salt.

18. A compound of claim 1, which is {4-[4-[(4-Fluorophenyl)phenylmethyl]piperazin-1-yl]-(E)-but-2-enyloxy}acetic acid or its pharmaceutically acceptable salt.

19. A pharmaceutical composition comprising compound of formula I as claimed in claim 1 and a pharmaceutically acceptable carrier.

* * * * *

UNITED STATES PATENT AND TRADEMARK OFFICE
CERTIFICATE OF CORRECTION

PATENT NO.       : 7,297,697 B2
APPLICATION NO.  : 10/509052
DATED            : November 20, 2007
INVENTOR(S)      : Midha et al.

It is certified that error appears in the above-identified patent and that said Letters Patent is hereby corrected as shown below:

Title page (57) Abstract, line 17: "either E or Z configuration;" should read --either *E* or *Z* configuration;--

Col. 1, line 40: "either E or Z configuration;" should read --either *E* or *Z* configuration;--

Col. 3, line 56: "either E or Z configuration;" should read --either *E* or *Z* configuration;--

Col. 4, line 53: "either E or Z configuration;" should read --either *E* or *Z* configuration;--

Col. 5, lines 15-30: Delete the incorrect compound and insert the correct compound below

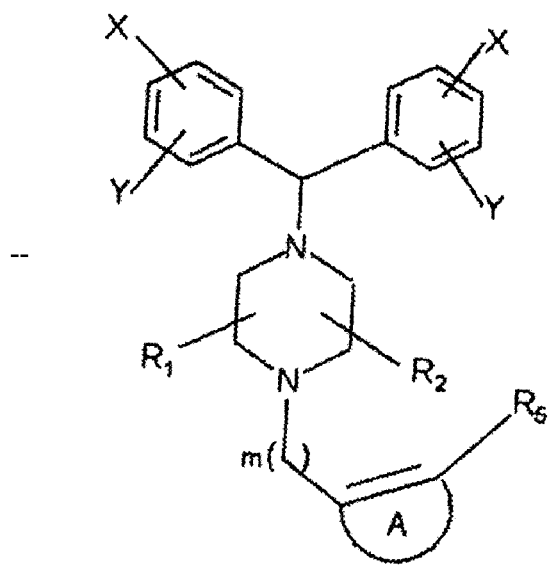

Col. 5, line 51: "are in E configuration," should read --are in *E* configuration,--

Col. 6, line 4: "in the E or Z configuration" should read --in the *E* or *Z* configuration--

Col. 7, line 18: "N-alkylated with" should read --*N*-alkylated with--

UNITED STATES PATENT AND TRADEMARK OFFICE
CERTIFICATE OF CORRECTION

| | | |
|---|---|---|
| PATENT NO. | : 7,297,697 B2 | Page 2 of 13 |
| APPLICATION NO. | : 10/509052 | |
| DATED | : November 20, 2007 | |
| INVENTOR(S) | : Midha et al. | |

It is certified that error appears in the above-identified patent and that said Letters Patent is hereby corrected as shown below:

Col. 7, line 20: "or p-toluenesulfonate" should read --or *p*-toluenesulfonate--

Col. 8, line 42: "N-alkylated with" should read --*N*-alkylated with--

Col. 8, line 44: : "or p-toluenesulfonate" should read --or *p*-toluenesulfonate--

Col. 9, line 65: "in E or Z configuration," should read --in *E* or *Z* configuration,--

Col. 11, line 54: "$R_4$ are in E" should read --$R_4$ are in *E*--

Col. 11, line 55: "by N-alkylating compound" should read --by *N*-alkylating compound--

Col. 14, lines 5-6: "4-{4-[Bis-(4-fluorophenyl)methyl]piperazin-1-yl}-(Z)-but-2-en-1-ol," should read --4-[4-[Bis-(4-fluorophenyl)methyl]piperazin-1-yl]-(*Z*)-but-2-en-1-ol,--

Col. 14, lines 10-11: "1-[bis-(4-fluorophenyl)methyl]piperazine (140g, 0.485mol), toluene (700ml), 4-chloro-2-butene-1-ol (67.25g, 0.631)," should read --1-[bis(4-fluorophenyl)methyl]piperazine (140 g, 0.485 mol), toluene (700 ml), (*Z*)-4-chloro-2-butene-1-ol (67.25 g, 0.631),--

Col. 14, lines 22-25: "(d, J=4.90Hz, 2H), 4.13 (d, J=3.96Hz, 2H), 4.20 (s, 1H), 5.55-5.75 (m, 1H), 5.75-6.00 (m, 1H), 6.96 (t, J=8.14Hz, 4H)," should read --(d, *J*=4.90 Hz, 2H), 4.13 (d, *J*=3.96 Hz, 2H), 4.20 (s, 1H), 5.55-5.75 (m, 1H), 5.75-6.00 (m, 1H), 6.96 (t, *J*=8.14 Hz, 4H),--

Col. 14, lines 30-31: "(R,S)-4-{4[(4-chlorophenyl)phenylmethyl]piperazin-1-yl}-(Z)-but-2-en-1-ol, [VIb(R,S)," should read --(*R,S*)-4-(4[(4-chlorophenyl)phenylmethyl]piperazin-1-yl]-(*Z*)-but-2-en-1-ol, [VIb(*R,S*),--

Col. 14, lines 35-37: "(R,S)-1-[(4-chlorophenyl)phenylmethyl]piperazine 8.0g (mol) is converted to (R,S)-4-{4-[(4-chlorophenyl)phenylmethyl]piperazin-1-yl}-(Z)-but-2-en-1-ol in a" should read --(*R,S*)-1-[(4-chlorophenyl)phenylmethyl]piperazine 8.0 g (mol) is converted to (*R,S*)-4-[4-[(4-chlorophenyl)phenylmethyl]piperazin-1-yl]-(*Z*)-but-2-en-1-ol in a--

UNITED STATES PATENT AND TRADEMARK OFFICE
CERTIFICATE OF CORRECTION

PATENT NO. : 7,297,697 B2
APPLICATION NO. : 10/509052
DATED : November 20, 2007
INVENTOR(S) : Midha et al.

It is certified that error appears in the above-identified patent and that said Letters Patent is hereby corrected as shown below:

Col. 14, line 43: "(J=5.75Hz, 2H), 4.13 (d, J=-5.25Hz, 2H)," should read --($J$=5.75Hz, 2H), 4.13 (d, $J$=-5.25Hz, 2H),--

Col. 14, line 49: "4-{4-Benzhydrylpiperazin-1-yl}-(Z)-but-2-en-1-ol," should read --4-[4-Benzhydrylpiperazin-1-yl]-($Z$)-but-2-en-1-ol,--

Col. 14, line 53: "toluene (20ml), 4-chloro-2-butene-1-ol" should read --toluene (20 ml), ($Z$)-4-chloro-2-butene-1-ol--

Col. 14, line 65: "(J=5.52Hz, 2H), 4.13 (dd, $J_1$=5.19Hz, $J_2$=0.68Hz, 2H)," should read --($J$=5.52Hz, 2H), 4.13 (dd, $J_1$=5.19Hz, $J_2$=0.68Hz, 2H),--

Col. 15, lines 3-4: "4-{4-[Bis-(2,4-difluorophenyl)methyl]piperazin-1-yl}-(Z)-but-2-en-1-ol," should read --4-[4-[Bis(2,4-difluorophenyl)methyl]piperazin-1-yl]-($Z$)-but-2-en-1-ol,--

Col. 15, lines 8-9: "is converted to 4-{4-[bis-(2,4-difluorophenyl)methyl]piperazin-1-yl}-(Z)-but-2-en-1-ol in a" should read --is converted to 4-[4-[bis(2,4-difluorophenyl)methyl]piperazin-1-yl]-($Z$)-but-2-en-1-ol in a--

Col. 15, line 15: "($J_1$=6.00Hz, $J_2$=0.74Hz, 2H), 4.14 (dd, $J_1$=5.31Hz, $J_2$=0.98" should read --($J_1$=6.00Hz, $J_2$=0.74Hz, 2H), 4.14 (dd, $J_1$=5.31Hz, $J_2$=0.98--

Col. 15, lines 20-21: "4-{4-[Bis-(4-chlorophenyl)methyl]piperazin-1-yl}-(Z)-but-2-en-1-ol," should read --4-[4-[Bis(4-chlorophenyl)methyl]piperazin-1-yl]-($Z$)-but-2-en-1-ol,--

Col. 15, lines 25-27: "1-[Bis-(4-chlorophenyl)methyl] piperazine (5.044g, mol) is converted to 4-{4-[bis-(4-chlorophenyl)methyl]piperazin-1-yl}-(Z)-but-2-en-1-ol in a" should read --1-[Bis(4-chlorophenyl)methyl]piperazine (5.044 g, mol) is converted to 4-[4-[bis(4-chlorophenyl)methyl]piperazin-1-yl]-($Z$)-but-2-en-1-ol in a--

Col. 15, line 32: "(J=5.87Hz, 2H), 4.13 (dd, $J_1$=5.26Hz, $J_2$=0.88, 2H)," should read --($J$=5.87Hz, 2H), 4.13 (dd, $J_1$=5.26Hz, $J_2$=0.88, 2H),--

Col. 15, lines 37-38: "{2-{4-[Bis-(4-fluorophenyl)methyl]piperazin-1-yl-methyl}phenyl}methanol" should read --[2-[4-[Bis(4-fluorophenyl)methyl]piperazin-1-yl-methyl]phenyl]methanol--

UNITED STATES PATENT AND TRADEMARK OFFICE
CERTIFICATE OF CORRECTION

PATENT NO.       : 7,297,697 B2
APPLICATION NO.  : 10/509052
DATED            : November 20, 2007
INVENTOR(S)      : Midha et al.

It is certified that error appears in the above-identified patent and that said Letters Patent is hereby corrected as shown below:

Col. 15, lines 41-43: "1-[Bis-(4-chlorophenyl)methyl]piperazine (5.0g, 0.0173mol ) is converted to {2-{4-[bis-(4-fluorophenyl)methyl]piperazin-1-ylmethyl}phenyl}methanol" should read --1-[Bis(4-chlorophenyl)methyl]piperazine (5.0 g, 0.0173 mol) is converted to [2-[4 [bis(4-fluorophenyl)methyl]piperazin-1-ylmethyl]phenyl]methanol--

Col. 15, lines 54-55: "{2-{4-[(4-chlorophenyl)phenylmethyl]piperazin-1-ylmethyl}phenyl}methanol," should read --[2-[4-[(4-chlorophenyl)phenylmethyl]piperazin-1-ylmethyl]phenyl]methanol,--

Col. 15, lines 58-60: "1-[Bis-(4-chlorophenyl)methyl]piperazine (4.0g, 0.0140mol) is converted to {2-{4-[(4-chlorophenyl)phenylmethyl]piperazin-1-ylmethyl}phenyl}methanol" should read --1-[Bis(4-chlorophenyl)methyl]piperazine (4.0 g, 0.0140 mol) is converted to [2-[4-[(4-chlorophenyl)phenylmethyl]piperazin-1-ylmethyl]phenyl]methanol--

Col. 16, lines 3-4: "4-{4-[Bis-(4-fluorophenyl)methyl]piperazin-1-yl}but-2-yn-1-ol" should read --4-[4-[Bis(4-fluorophenyl)methyl]piperazin-1-yl]but-2-yn-1-ol--

Col. 16, line 9: "To a solution containing 1-[bis-(4-fluorophenyl)methyl]" should read --To a solution containing 1-[bis(4-fluorophenyl)methyl]--

Col. 16, lines 25-26: "(t, J=1.84 Hz, 2H), 4.21 (s, 1H), 4.29 (t, J=1.80 Hz, 2H)," should read --(t, $J$=1.84 Hz, 2H), 4.21 (s, 1H), 4.29 (t, $J$=1.80 Hz, 2H),--

Col. 16, line 35: "0-5°C. for 1hr the temperature" should read --0-5°C. the temperature--

Col. 16, lines 56-57: "(R,S)-4-{4-[(4-Chlorophenyl)phenylmethyl]piperazin-1-yl}but-2-yn-1-ol" should read --($R,S$)-4-[4-[(4-Chlorophenyl)phenylmethyl]piperazin-1-yl]but-2-yn-1-ol--

Col. 16, line 60: "containing (R,S)-1-[(4-chlorophenyl)" should read --containing ($R,S$)-1-[(4-chlorophenyl)--

UNITED STATES PATENT AND TRADEMARK OFFICE
CERTIFICATE OF CORRECTION

PATENT NO.       : 7,297,697 B2
APPLICATION NO.  : 10/509052
DATED            : November 20, 2007
INVENTOR(S)      : Midha et al.

It is certified that error appears in the above-identified patent and that said Letters Patent is hereby corrected as shown below:

Col. 17, line 6: "(t, J=1.72Hz, 2H), 4.20 (s, 1H), 4.29 (t, J=1.63Hz," should read --(t, $J$=1.72Hz, 2H), 4.20 (s, 1H), 4.29 (t, $J$=1.63Hz,--

Col. 17, lines 11-12: "(R,S)-4-{4-[(4-fluorophenyl)phenylmethyl]piperazin-1-yl}but-2-yn-1-ol" should read --($R,S$)-4-[4-[(4-fluorophenyl)phenylmethyl]piperazin-1-yl]but-2-yn-1-ol--

Col. 17, line 40: "3.30 (t, J=1.83 Hz, 2H), 4.21 (s, 1H), 4.29 (t, J=1.78 Hz," should read --3.30 (t, $J$=1.83 Hz, 2H), 4.21 (s, 1H), 4.29 (t, $J$=1.78 Hz,--

Col. 17, lines 44-45: "4-{4-[Bis-(4-fluorophenyl)methyl]piperazin-1-yl)-(E)-but-2-en-1-ol," should read --4-[4-[Bis(4-fluorophenyl)methyl]piperazin-1-yl]-($E$)-but-2-en-1-ol,--

Col. 17, lines 49-50: "methyl 4-{4-[bis-(4-fluorophenyl)methyl]piperazin-1-yl}-(E)-but-2-enoate" should read --methyl 4-[4-[bis(4-fluorophenyl)methyl]piperazin-1-yl]-($E$)-but-2-enoate--

Col. 17, line 54: "for further 1.0 hrs at" should read --for further 1.0 hr at--

Col. 18, line 2: "(d, J=5.38 Hz, 2H), 4.12 (d, J=4.40" should read --(d, $J$=5.38 Hz, 2H), 4.12 (d, $J$=4.40--

Col. 18, lines 9-10: "4-{4-[Bis-(4-fluorophenyl)methyl]piperazin-1-yl}-(E)-but-2-en-1-ol" should read --4-[4-[Bis(4-fluorophenyl)methyl]piperazin-1-yl]-($E$)-but-2-en-1-ol--

Col. 18, lines 14-15: "4-{4-[bis-(4-fluorophenyl)methyl]piperazin-1-yl}but-2-yn-1-ol" should read --4-[4-[bis(4-fluorophenyl)methyl]piperazin-1-yl]but-2-yn-1-ol--

Col. 18, line 26: "(d, J=4.91 Hz, 2H), 4.11 (d, J=3.71" should read --(d, $J$=4.91 Hz, 2H), 4.11 (d, $J$=3.71--

Col. 18, lines 32-33: "(R,S)-4-{14[(4-chlorophenyl)phenylmethyl]piperazin-1-yl}-(E)-but-2-en-1-ol," should read --($R,S$)-4-[4-[(4-chlorophenyl)phenylmethyl]piperazin-1-yl]-($E$)-but-2-en-1-ol,--

UNITED STATES PATENT AND TRADEMARK OFFICE
CERTIFICATE OF CORRECTION

PATENT NO. : 7,297,697 B2
APPLICATION NO. : 10/509052
DATED : November 20, 2007
INVENTOR(S) : Midha et al.

It is certified that error appears in the above-identified patent and that said Letters Patent is hereby corrected as shown below:

Col. 18, lines 37-38: "(R,S)-4-{4-[(4-chlorophenyl)phenylmethyl]piperazin-1-yl}but-2-yn-1-ol (3.5g, mol) is converted to (R,S)-4-{4-[(4-chlorophenyl)phenylmethyl]piperazin-1-yl}-(E)-but-2-en-1-ol in a" should read --(*R,S*)-4-[4-[(4-chlorophenyl)phenylmethyl]piperazin-1-yl]but-2-yn-1-ol (3.5 g, mol) is converted to (*R,S*)-4-[4-[(4-chlorophenyl)phenylmethyl]piperazin-1-yl]-(*E*)-but-2-en-1-ol in a--

Col. 18, line 45 "(J=4.83 Hz, 2H), 4.11 (d, J=3.52 Hz, 2H)," should read --(*J*=4.83 Hz, 2H), 4.11 (d, *J*=3.52 Hz, 2H),--

Col. 18, lines 50-51: "(R,S)-4-{4-[(4-fluorophenyl)phenylmethyl]piperazin-1-yl}-(E)-but-2-en-1-ol" should read ----(*R,S*)-4-[4-[(4-fluorophenyl)phenylmethyl]piperazin-1-yl]-(*E*)-but-2-en-1-ol--

Col. 18, lines 55-58: "(R,S)-4-{4-[(4-fluorophenyl)phenylmethyl]piperazin-1-yl}but-2-yn-1-ol (2.13g, 0.0063 mol) is converted to (R,S)-4-{4-[(4-fluorophenyl)phenylmethyl]piperazin-1-yl}-(*E*)-but-2-en-1-ol in a" should read --(*R,S*)-4-[4-[(4-fluorophenyl)phenylmethyl]piperazin-1-yl]but-2-yn-1-ol (2.13 g, 0.0063 mol) is converted to --(*R,S*)-4-[4-[(4-fluorophenyl)phenyl-methyl]piperazin-1-yl]-(*E*)-but-2-en-1-ol in a--

Col. 18, lines 65-66: "d, J=5.23 Hz, 2H), 4.11 (d, J=4.20 Hz, 211)," should read --(d, *J*=5.23 Hz, 2H), 4.11 (d, *J*=4.20 Hz, 211),--

Col. 19, lines 3-4: "Methyl 4-{4-[Bis-(4-fluorophenyl)methyl]piperazin-1-yl}-(E)-but-2-enoate," should read --Methyl 4-[4-[Bis(4-fluorophenyl)methyl]piperazin-1-yl]-(E)-but-2-enoate,--

Col. 19, line 7: "solution of methyl-4-bromocrotonate" should read --solution of methyl 4-bromocrotonate--

Col. 19, line 9: "containing 1-[bis-(4-fluorophenyl)methyl]piperazine" should read --containing 1-[bis(4-fluorophenyl)methyl]piperazine--

Col. 19, line 25: "(d, J=5.00 Hz, 2H)," should read --d, *J*=5.00 Hz, 2H),--

UNITED STATES PATENT AND TRADEMARK OFFICE
CERTIFICATE OF CORRECTION

PATENT NO. : 7,297,697 B2
APPLICATION NO. : 10/509052
DATED : November 20, 2007
INVENTOR(S) : Midha et al.

It is certified that error appears in the above-identified patent and that said Letters Patent is hereby corrected as shown below:

Col. 19, lines 32-33: "Methyl 4-{4-[(4-chlorophenyl)phenylmethyl]piperazin-1-yl}-(E)-but-2-enoate," should read --Methyl --4-[4-[(4-chlorophenyl)phenylmethyl]piperazin-1-yl]-(*E*)-but-2-enoate,--

Col. 19, line 35: "containing (R,S)-1-[(4-chlorophenyl)" should read --containing (*R,S*)-1-[(4-chlorophenyl)--

Col. 19, lines 36-37: "methyl-4-bromocrotonate" should read --methyl 4-bromocrotonate--

Col. 19, line 46: "($J_1$=6.20 Hz, $J_2$=1.39 Hz, 2H)," should read --(*$J_1$*=6.20 Hz, *$J_2$*=1.39 Hz, 2H),--

Col. 19, lines 52-53: "{4-{4-[Bis-(4-fluorophenyl)methyl]-piperazin-1-yl)-(Z)-but-2-enyloxy}acetic acid" should read --[4-[4-Bis(4-fluorophenyl)methyl]-piperazin-1-yl]-(*Z*)-but-2-enyloxy]acetic acid--

Col. 19, lines 55-56: "solution of 4-{4-[bis-(4-fluorophenyl)methyl]piperazin-1-yl}-(Z)-but-2-en-1-ol" should read --4-[4-[bis(4-fluorophenyl)methyl]piperazin-1-yl]-(*Z*)-but-2-en-1-ol--

Col. 19, line 57: "tert-butoxide" should read --*tert*-butoxide--

Col. 19, line 58: "tert-butanol" should read --*tert*-butanol--

Col. 19, line 62: "tert-butanol" should read --*tert*-butanol--

Col. 20, lines 4-5: "(d, J=7.51 Hz, 2), 3.96 (s, 2H), 4.19 (d, J=4.51 Hz, 2)," should read --(d, *J*=7.51 Hz, 2H), 3.96 (s, 2H), 4.19 (d, *J*=4.51 Hz, 2H),--

Col. 20, lines 7-8: "suspension of {4-[4-[bis-(4-fluorophenyl)methyl]piperazin-1-yl]-(Z)-but-2-enyloxy}acetic acid" should read --suspension of [4-[4-[bis(4-fluorophenyl)methyl]piperazin-1-yl]-(*Z*)-but-enyloxy]acetic acid--

Col. 20, lines 17-18: "(R,S)-4-[4-[(4-Chlorophenyl)phenylmethyl]piperazin-1 yl]-(Z)-but-2-enyloxy}acetic acid dihydrochloride, [Ib, (R,S)]" should read --(*R,S*)-4-[4-[(4-Chlorophenyl)phenylmethyl]piperazin-1-yl]-(*Z*)-but-2-enyloxy]acetic acid dihydrochloride, [Ib (*R,S*)]--

UNITED STATES PATENT AND TRADEMARK OFFICE
CERTIFICATE OF CORRECTION

PATENT NO. : 7,297,697 B2
APPLICATION NO. : 10/509052
DATED : November 20, 2007
INVENTOR(S) : Midha et al.

It is certified that error appears in the above-identified patent and that said Letters Patent is hereby corrected as shown below:

Col. 20, lines 21-24: "(R,S)-4-{4-[(4-chlorophenyl)phenylmethyl]piperazin-1-yl}-(Z)-but-2-en-1-ol (100.0 g, 0.28 mol) is converted to (R,S)-{4-[4-[(4-chlorophenyl)phenylmethyl]piperazin-1-yl]-(Z)-but-2-enyloxy}acetic acid" should read --(*R,S*)-4-[4-[(4-chlorophenyl)phenylmethyl]piperazin-1-yl]-(*Z*)-but-2-en-1-ol (100.0 g, 0.28 mol) is converted to (*R,S*)-[4-[4-[(4-chlorophenyl)phenylmethyl]piperazin-1-yl]-(*Z*)-but-2-enyloxy]acetic acid--

Col. 20, line 30: "d, J=7.43 Hz, 2H)," should read --(d, *J*=7.43 Hz, 2H),--

Col. 20, line 37: "(Z)-but-2-enyloxy]" should read --(*Z*)-but-2-enyloxy]--

Col. 20, line 40: "4-(4-Benzhydrylpiperazin-1-yl)-(Z)-but-2-en-1-ol" should read --4-(4-Benzhydrylpiperazin-1-yl)-(*Z*)-but-2-en-1-ol--

Col. 20, line 42: "yl)-(Z)-but-2-enyloxy]acetic" should read --yl-(*Z*)-but-2-enyloxy]acetic--

Col. 20, lines 49-50: "d, J=7.53 Hz, 2H), 3.96 (s, 2H), 4.18 (d, J= 4.60 Hz, 2H)," should read --(d, *J*=7.53 Hz, 2H), 3.96 (s, 2H), 4.18 (d, *J*= 4.60 Hz, 2H),--

Col. 20, lines 56-57: "{4-[Bis-(2,4-difluorophenyl)methyl]-piperazin-1-yl}-(Z)-but-2-enyloxy}acetic Acid Dihydrochloride," should read --[4-[Bis(2,4-difluorophenyl)methyl]-piperazin-1-yl]-(*Z*)-but-2-enyloxy]acetic acid dihydrochloride,--

Col. 20, lines 60-63: "4-{4-[Bis-(2,4-difluorophenyl)methyl]piperazin-1-yl}-(Z)-but-2-en-1-ol (6.2 g, 0.0157 mol) is converted {4-{4-[bis-(2,4-difluorophenyl)methyl]-piperazin-1-yl}-(Z)-but-2-enyloxy}acetic acid" should read --4-[4-[Bis(2,4-difluorophenyl)methyl]piperazin-1-yl]-(*Z*)-but-2-en-1-ol (6.2 g, 0.0157 mol) is converted [4-[4-[bis(2,4-difluorophenyl)methyl]-piperazin-1-yl]-(*Z*)-but-2-enyloxy]acetic acid--

Col. 21, lines 2-3: "(d, J=6.07 Hz, 2H), 3.96 (s, 2H), 4.17 (d, J=3.90 Hz, 2H)," should read --(d, *J*=6.07 Hz, 2H), 3.96 (s, 2H), 4.17 (d, *J*=3.90 Hz, 2H),--

Col. 21, lines 13-14: "{4-[4-[Bis-(4-chlorophenyl)methyl]-piperazin-1-yl]-(Z)-but-2-enyloxy}acetic acid" should read --[4-[4-[Bis(4-chlorophenyl)methyl]piperazin-1-yl]-(*Z*)-but-2-enyloxy]acetic acid--

UNITED STATES PATENT AND TRADEMARK OFFICE
CERTIFICATE OF CORRECTION

PATENT NO. : 7,297,697 B2
APPLICATION NO. : 10/509052
DATED : November 20, 2007
INVENTOR(S) : Midha et al.

It is certified that error appears in the above-identified patent and that said Letters Patent is hereby corrected as shown below:

Col. 21, lines 16-19: "4-{4-[Bis-(4-chlorophenyl)methyl]piperazin-1-yl}-(Z)-but-2-en-1-ol (2.26 g, mol) is converted to {4-[4-[bis-(4-chlorophenyl)methyl]-piperazin-1-yl}-(Z)-but-2-enyloxy}acetic acid" should read --4-[4-[Bis(4-chlorophenyl)methyl]piperazin-1-yl]-(Z)-but-2-en-1-ol (2.26 g, mol) is converted to [4-[4-[bis(4-chlorophenyl)methyl]-piperazin-1-yl]-(Z)-but-2-enyloxy]acetic acid--

Col. 21, lines 25-26: "(d, J=7.38 Hz, 2H), 3.94 (s, 2H), 4.20 (d, J=4.08 Hz, 2H)," should read --(d, $J$=7.35 Hz, 2H), 3.94 (s, 2H), 4.20 (d, $J$=4.08 Hz, 2H),--

Col. 21, lines 34-35: "{c4-{4-[Bis-(4-fluorophenyl)methyl]-piperazin-1-yl}-(Z)-but-2-enyloxy}acetic acid" should read --[4-[4-[Bis(4-fluorophenyl)methyl]-piperazin-1-yl]-(Z)-but-2-enyloxy]acetic acid--

Col. 21, lines 39-40: "solution of {4-{4-[bis-(4-fluorophenyl)methyl]-piperazin-1-yl}-(Z)-but-2-enyloxy}acetic acid" should read --solution of [4-[4-[bis(4-fluorophenyl)methyl]-piperazin-1-yl]-(Z)-but-2-enyloxy]acetic acid--

Col. 21, line 47: "(d, J=7.66 Hz, 2H)," should read --(d, $J$=7.66 Hz, 2H),--

Col. 21, lines 54-55: "{4-{4-[Bis-(4-fluorophenyl)methyl]-piperazin-1-yl}-(Z)-but-2-enyloxy}acetic acid" should read --[4-[4-[Bis(4-fluorophenyl)methyl]-piperazin-1-yl]-(Z)-but-2-enyloxy]acetic acid--

Col. 21, lines 58-59: "solution of {4-{4-[bis-(4-fluorophenyl)methyl]-piperazin-1-yl}-(Z)-but-2-enyloxy}acetic acid" should read --solution of [4-[4-[bis(4-fluorophenyl)methyl]-piperazin-1-yl]-(Z)-but-2-enyloxy]acetic acid--

Col. 21, lines 65-66: "(t, J=7.10 Hz, 3H), 2.70-4.30 (m, 17H), 5.70-6.20 (m, 2H), 7.10 (t, J=8.62" should read --(t, $J$=7.10 Hz, 3H), 2.70-4.30 (m, 17H), 5.70-6.20 (m, 2H), 7.10 (t, $J$=8.62--

Col. 22, lines 3-4: "{4-{4-[Bis-(4-fluorophenyl)methyl]-piperazin-1-yl}-(Z)-but-2-enyloxy}acetic acid" should read --[4-[4-[Bis(4-fluorophenyl)methyl]-piperazin-1-yl]-(Z)-but-2-enyloxy]acetic acid--

Col. 22, lines 7-8: "solution of {4-{4-[bis-(4-fluorophenyl)methyl]piperazin-1-yl}-(Z)-but-2-enyloxy}acetic acid" should read --[4-[4-[bis(4-fluorophenyl)methyl]piperazin-1-yl]-(Z)-but-2-enyloxy]acetic acid--

UNITED STATES PATENT AND TRADEMARK OFFICE
CERTIFICATE OF CORRECTION

PATENT NO. : 7,297,697 B2
APPLICATION NO. : 10/509052
DATED : November 20, 2007
INVENTOR(S) : Midha et al.

It is certified that error appears in the above-identified patent and that said Letters Patent is hereby corrected as shown below:

Col. 22, line 15: "(d, J=6.25 Hz," should read --(d, $J$=6.25 Hz,--

Col. 22, line 17: "(t, J=8.56" should read --(t, $J$=8.56--

Col. 22, lines 22-24: "(R,S)-{4-14[(4-chlorophenyl)phenylmethyl]piperazin-1-yl]-(Z)-but-2-enyloxy}acetic Acid Isopropyl Ester Dihydrochloride, (Ii):" should read --($R,S$)-[4-[4[(4-chlorophenyl)phenylmethyl]piperazin-1-yl]-($Z$)-but-2-enyloxy]acetic acid isopropyl ester dihydrochloride, (Ii)--

Col. 22, lines 26-28: "using (R,S)-{4-[4-[(4-chlorophenyl)phenylmethyl]piperazin-1-yl]-(Z)-but-2-enyloxy}acetic acid" should read --using ($R,S$)-[4-[4-[(4-chlorophenyl)phenylmethyl]piperazin-1-yl]-($Z$)-but-2-enyloxy]acetic acid--

Col. 22, lines 29-30: "(d, J=6.26 Hz, 6H), 2.80-3.70 (m, 8H), 3.80-4.15 (m, 3H), 4.21 (d, J=5.57" should read --(d, $J$=6.26 Hz, 6H), 2.80-3.70 (m, 8H), 3.80-4.15 (m, 3H), 4.21 (d, $J$=5.57--

Col. 22, lines 36-37: "(R,S)-{4-[4-[(4-chlorophenyl)phenylmethyl]piperazin-1-yl]-(Z)-but-2-enyloxy}acetic acid" should read --($R,S$)-[4-[4-[(4-chlorophenyl)phenylmethyl]piperazin-1-yl]-($Z$)-but-2-enyloxy]acetic acid--

Col. 22, lines 40-41: "solution of (R,S)-{4-[4-[(4-chlorophenyl)phenylmethyl]piperazin-1-yl]-(Z)-but-2-enyloxy}acetic" should read --solution of ($R,S$)-[4-[4-[(4-chlorophenyl)phenylmethyl]piperazin-1-yl]-($Z$)-but-2-enyloxy]acetic--

Col. 22, line 55-57: "(R,S)-{4-[4-[(4-chlorophenyl)phenylmethyl]piperazin-1-yl]-(Z)-but-2-enyloxy}acetic Acid Ethyl Ester Dihydrochloride," should read --($R,S$)-[4-[4-[(4-chlorophenyl)phenylmethyl]piperazin-1-yl]-($Z$)-but-2-enyloxy]acetic acid ethyl ester dihydrochloride,--

Col. 22, lines 60-62: "using (R,S)-{4-[4-[(4-chlorophenyl)phenylmethyl]piperazin-1-yl]-(Z)-but-2-enyloxy}acetic acid" should read --using ($R,S$)-[4-[4-[(4-chlorophenyl)phenylmethyl]piperazin-1-yl]-($Z$)-but-2-enyloxy]acetic acid--

UNITED STATES PATENT AND TRADEMARK OFFICE
CERTIFICATE OF CORRECTION

PATENT NO. : 7,297,697 B2
APPLICATION NO. : 10/509052
DATED : November 20, 2007
INVENTOR(S) : Midha et al.

It is certified that error appears in the above-identified patent and that said Letters Patent is hereby corrected as shown below:

Col. 22, line 64: "(t, J=7.12 Hz," should read --(t, *J*=7.12 Hz,--

Col. 23, lines 3-4: "{2-{4-[bis-(4-fluorophenyl)methyl]piperazin-1-ylmethyl}benzyloxy}acetic acid" should read --[2-[4-[bis(4-fluorophenyl)methyl]piperazin-1-ylmethyl]benzyloxy]acetic acid--

Col. 23, lines 7-10: "{2-{4-[Bis-(4-fluorophenyl)methyl]piperazin-1-ylmethyl}phenyl}methanol (5.0 g, 0.0122 mol) is converted to {2-{4-[Bis-(4-fluorophenyl)methyl]piperazin-1-ylmethyl}benzyloxy}acetic acid" should read --[2-[4-[Bis(4-fluorophenyl)methyl]piperazin-1-ylmethyl]phenyl]methanol (5.0 g, 0.0122 mol) is converted to [2-[4-[bis(4-fluorophenyl)methyl]piperazin-1-ylmethyl]benzyloxy]acetic acid--

Col. 23, lines 26-27: "(R,S) {2-{4-[(4-chlorophenyl)phenylmethyl]piperazin-1-ylmethyl}benzyloxy}acetic acid" should read --(*R,S*) [2-[4-[(4-chlorophenyl)phenylmethyl]piperazin-1-ylmethyl]benzyloxy]acetic acid--

Col. 23, lines 30-33: "{2-{4-[(4-chlorophenyl)phenylmethyl]piperazin-1-ylmethyl}phenyl}methanol (4.0 g, 9.83 mmol) is converted to {2-{4-[(4-chlorophenyl)phenylmethyl]piperazin-1-ylmethyl}benzyloxy}acetic acid" should read --[2-[4-[(4-chlorophenyl)phenylmethyl]piperazin-1-ylmethyl]phenyl]methanol (4.0 g, 9.83 mmol) is converted to [2-[4-[(4-chlorophenyl)phenylmethyl]piperazin-1-ylmethyl]benzyloxy]acetic acid--

Col. 23, lines 46-47: "{4-[4-[Bis-(4-fluorophenyl)methyl]piperazin-1-yl]-(E)-but-2-enyloxy}acetic acid" should read --[4-[4-[Bis(4-fluorophenyl)methyl]piperazin-1-yl]-(*E*)-but-2-enyloxy]acetic acid--

Col. 23, lines 51-54: "solution of 4-{4-[bis-(4-fluorophenyl)methyl]piperazin-1-yl}-(E)-but-2-en-1-ol (247.0 g, 0.689 mol) and potassium tert-butoxide (139.2g, 1.240mol) in anhydrous tert-butanol" should read --solution of 4-[4-[bis(4-fluorophenyl)methyl]piperazin-1-yl]-(*E*)-but-2-en-1-ol (247.0 g, 0.689 mol) and potassium *tert*-butoxide (139.2 g, 1.240 mol) in anhydrous *tert*-butanol--

Col. 23, line 58: "until tert-butanol is" should read --until *tert*-butanol is--

UNITED STATES PATENT AND TRADEMARK OFFICE
CERTIFICATE OF CORRECTION

PATENT NO. : 7,297,697 B2
APPLICATION NO. : 10/509052
DATED : November 20, 2007
INVENTOR(S) : Midha et al.

It is certified that error appears in the above-identified patent and that said Letters Patent is hereby corrected as shown below:

Col. 24, line 2: "J=6.79 Hz, 2H)" should read --$J$=6.79 Hz, 2H)--

Col. 24, lines 8-9: "(R,S)-{4-[4-[(4-Chlorophenyl)phenylmethyl]piperazin-1-yl]-(E)-but-2-enyloxy}acetic acid" should read --($R,S$)-[4-[4-[(4-Chlorophenyl)phenylmethyl]piperazin-1-yl]-($E$)-but-2-enyloxy]acetic acid--

Col. 24, lines 12-15: "(R,S)-4-{4-[(4-Chlorophenyl)phenylmethyl]piperazin-1-yl}-(E)-but-2-en-1-ol (1.9 g, 0.0053 mol) is converted to (R,S)-{4-[4-[(4-Chlorophenyl)phenylmethyl]piperazin-1-yl]-(E)-but-2-enyloxy}acetic acid" should read --($R,S$)-4-[4-[(4-Chlorophenyl)phenylmethyl]piperazin-1-yl]-($E$)-but-2-en-1-ol (1.9 g, 0.0053 mol) is converted to ($R,S$)-[4-[4-[(4-Chlorophenyl)phenylmethyl]piperazin-1-yl]-($E$)-but-2-enyloxy]acetic acid--

Col. 24, lines 27-28: "(R,S)-{4-[4-[(4-fluorophenyl)phenylmethyl]piperazin-1-yl]-(E)-but-2-enyloxy}acetic acid" should read --($R,S$)-[4-[4-[(4-fluorophenyl)phenylmethyl]piperazin-1-yl]-($E$)-but-2-enyloxy]acetic acid--

Col. 24, lines 31-34: "(R,S)-4-{4-[(4-Fluorophenyl)phenylmethyl]piperazin-1-yl}-(E)-but-2-en-1-ol (0.7 g, 2.06 mmol) is converted to (R,S)-{4-[4-[(4-fluorophenyl)phenylmethyl]piperazin-1-yl]-(E)-but-2-enyloxy}acetic acid" should read --($R,S$)-4-[4-[(4-Fluorophenyl)phenylmethyl]piperazin-1-yl}-($E$)-but-2-en-1-ol (0.7 g, 2.06 mmol) is converted to ($R,S$)-[4-[4-[(4-fluorophenyl)phenylmethyl]piperazin-1-yl]-($E$)-but-2-enyloxy]acetic acid--

Col. 25, line 55, claim 1: "or cyclo)," should read --or cyclic),--

Col. 25, line 58, claim 1: "or cyclo)," should read --or cyclic),--

UNITED STATES PATENT AND TRADEMARK OFFICE
CERTIFICATE OF CORRECTION

PATENT NO. : 7,297,697 B2
APPLICATION NO. : 10/509052
DATED : November 20, 2007
INVENTOR(S) : Midha et al.

It is certified that error appears in the above-identified patent and that said Letters Patent is hereby corrected as shown below:

Col. 26, line 2, claim 1: "either E or Z configuration;" should read --either $E$ or $Z$ configuration;--

Col. 26, line 41, claim 1: "or cyclo)," should read --or cyclic),--

Signed and Sealed this

Nineteenth Day of August, 2008

JON W. DUDAS
*Director of the United States Patent and Trademark Office*